United States Patent
Zurovcik

(10) Patent No.: US 11,786,410 B2
(45) Date of Patent: Oct. 17, 2023

(54) MODIFIABLE OCCLUSIVE SKIN DRESSING

(71) Applicant: Worldwide Innovative Healthcare, Inc., Cambridge, MA (US)

(72) Inventor: Danielle R. Zurovcik, Cambridge, MA (US)

(73) Assignee: WORLDWIDE INNOVATIVE HEALTH CARE, INC., Cambridge, MA (US)

(*) Notice: Subject to any disclaimer, the term of this patent is extended or adjusted under 35 U.S.C. 154(b) by 216 days.

(21) Appl. No.: 17/020,474

(22) Filed: Sep. 14, 2020

(65) Prior Publication Data
US 2021/0030597 A1    Feb. 4, 2021

Related U.S. Application Data

(63) Continuation of application No. 14/929,146, filed on Oct. 30, 2015, now abandoned, which is a
(Continued)

(51) Int. Cl.
*A61F 13/00* (2006.01)
*A61B 46/00* (2016.01)
(Continued)

(52) U.S. Cl.
CPC ........ *A61F 13/00068* (2013.01); *A61B 46/00* (2016.02); *A61F 13/0216* (2013.01);
(Continued)

(58) Field of Classification Search
CPC ............ A61F 2013/00536; A61F 5/445; A61F 13/00068; A61F 13/0216; A61F 13/0226; A61F 2013/00268; A61F 2013/00412; A61B 2019/307; A61B 17/085; A61B 2046/205; A61B 2217/005; A61B 2050/006; A61B 2050/0065; A61B 2050/314; A61B 46/00; A61B 50/30; A61B 17/0057; A61B 19/026; A61B 19/08;
(Continued)

(56) References Cited

U.S. PATENT DOCUMENTS 5,636,643 A * 6/1997 Argenta ................ A61M 1/90
602/42
5,860,420 A * 1/1999 Wiedner ................ A61B 46/00
128/853
(Continued)

OTHER PUBLICATIONS www.smooth-on.com : (skin_tite_sealant_-_Google_Search.pdf) (Year: 2010).*
(Continued)

*Primary Examiner* — Caitlin A Carreiro
(74) *Attorney, Agent, or Firm* — Douglas Denningen

(57) ABSTRACT

Occlusive tissue dressings and methods including an elastomeric drape and a liquid component, at least partially cross-linked at least after one of drying and curing, suitable for application at a dressing-to-skin interface in order to create a substantially air-tight seal. The same or a different liquid component may be applied by a user at a tube-to-dressing interface in order to create a similar air-tight seal around the tube, if not occlusively sealed during its manufacture.

36 Claims, 19 Drawing Sheets

Related U.S. Application Data continuation of application No. 13/745,690, filed on Jan. 18, 2013, now Pat. No. 9,173,777.

(60) Provisional application No. 61/588,121, filed on Jan. 18, 2012.

(51) Int. Cl.
  *A61F 13/02* (2006.01)
  *A61M 1/00* (2006.01)
  *A61B 17/08* (2006.01)
  *A61B 46/20* (2016.01)

(52) U.S. Cl.
  CPC ...... *A61F 13/0226* (2013.01); *A61F 13/0246* (2013.01); *A61F 13/0253* (2013.01); *A61F 13/0259* (2013.01); *A61M 1/682* (2021.05); *A61M 1/80* (2021.05); *A61M 1/82* (2021.05); *A61M 1/915* (2021.05); *A61B 17/085* (2013.01); *A61B 2046/205* (2016.02); *A61B 2217/005* (2013.01); *A61F 2013/0017* (2013.01); *A61F 2013/00174* (2013.01); *A61F 2013/00268* (2013.01); *A61F 2013/00412* (2013.01); *A61F 2013/00536* (2013.01); *A61F 2013/00702* (2013.01); *A61M 1/92* (2021.05)

(58) Field of Classification Search
  CPC .......... A61B 17/10; A61B 2017/00526; A61B 2019/0267; A61B 2019/085; A61M 25/02; A61M 25/04; A61M 5/002; A61M 1/0088; A61M 1/0011; A61M 1/0066; A61M 1/0072; Y10S 526/943; B32B 27/06; B32B 3/02; B32B 2250/44; B32B 2307/7265; B32B 2307/748; B32B 2405/00; B32B 2535/00; B32B 2556/00; B32B 29/002; B32B 29/02; B32B 3/266; B32B 7/05; B32B 7/06; B32B 7/12; B65D 2205/02; B65D 2575/58; B65D 75/305; B65D 75/5805; B65D 75/5816; B65D 75/5855; B65D 75/5894; B65D 81/3453; C09D 133/20; A61L 15/58; A61L 15/24; A61L 26/0014; A61L 15/44; A61L 2300/404; A61L 26/0066; A61L 24/00; A61L 2/26; C08L 35/04; C08L 2666/02; C08L 57/02; C08L 2203/02; C09J 123/10; C09J 123/12; C09J 2201/606; C09J 2201/622; C09J 2205/31; C09J 2401/006; C09J 2421/00; C09J 2423/006; C09J 2423/046; C09J 2423/106; C09J 2427/006; C09J 2433/00; C09J 5/00; C09J 7/02
  USPC .............................. 128/849–856; 602/41, 54
  See application file for complete search history.

(56) References Cited

U.S. PATENT DOCUMENTS

| | | | |
|---|---|---|---|
| 6,874,657 B2 * | 4/2005 | Metzner | A61B 17/00491 222/391 |
| 2006/0030790 A1 * | 2/2006 | Braig | A61B 5/150274 600/584 |
| 2006/0195993 A1 * | 9/2006 | O'Neill | A47L 25/005 15/104.002 |
| 2007/0077156 A1 * | 4/2007 | Orr | F04B 7/02 417/395 |
| 2007/0147947 A1 * | 6/2007 | Stenton | A61M 35/006 401/133 |
| 2009/0044895 A1 * | 2/2009 | Fortune | A61L 31/129 156/60 |
| 2009/0152137 A1 * | 6/2009 | Estes | A61B 50/30 128/849 |
| 2010/0137775 A1 * | 6/2010 | Hu | A61M 1/915 602/54 |
| 2010/0228205 A1 * | 9/2010 | Hu | A61M 1/90 604/319 |

OTHER PUBLICATIONS www.smooth-on.com : (skin_tite_product_information.PDF) (Year: 2010).* www.smooth-on.com : (skin_tite. PDF) (Year: 2010).*

* cited by examiner

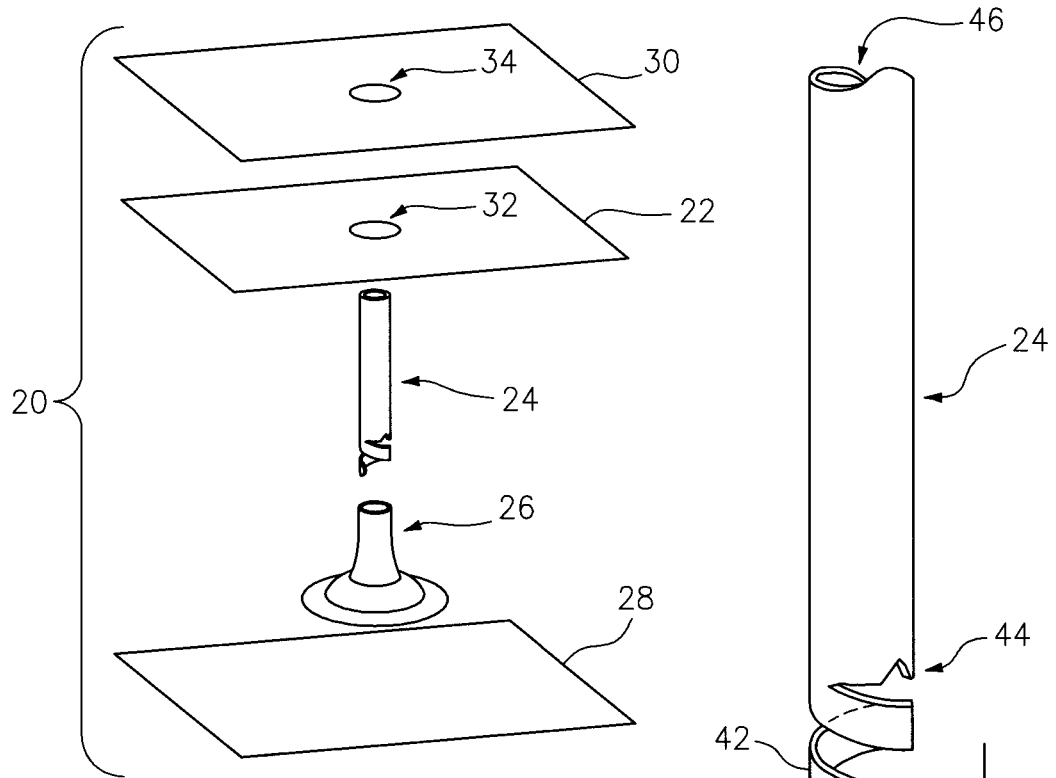
FIG. 1
FIG. 2
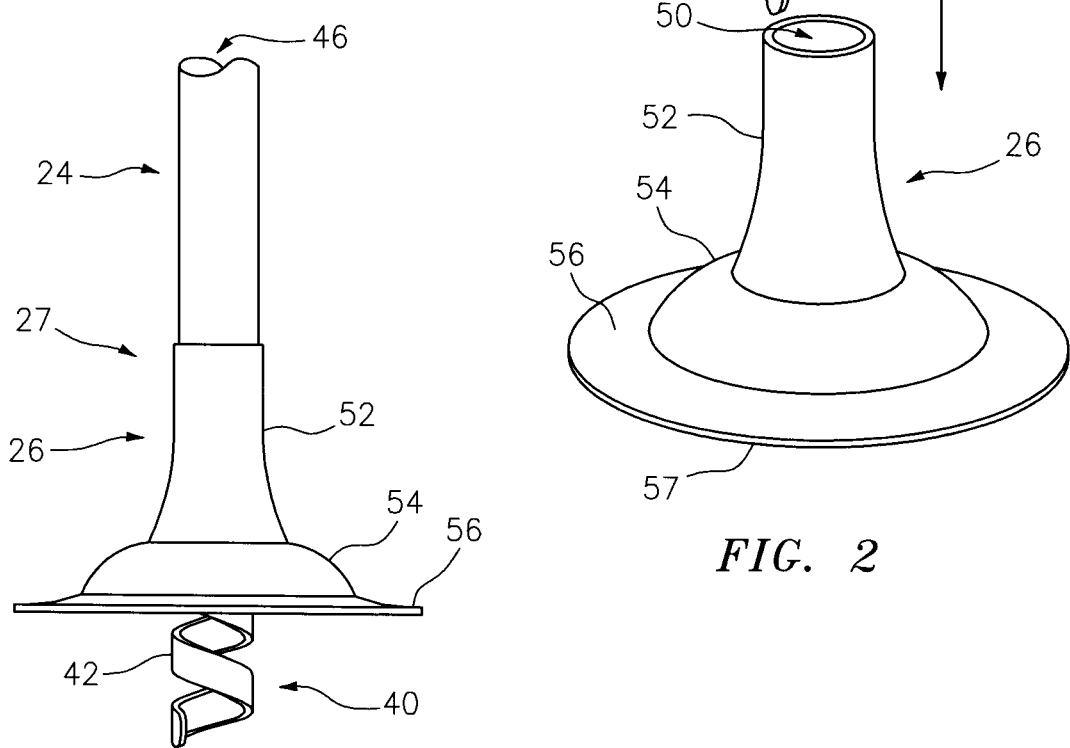
FIG. 3

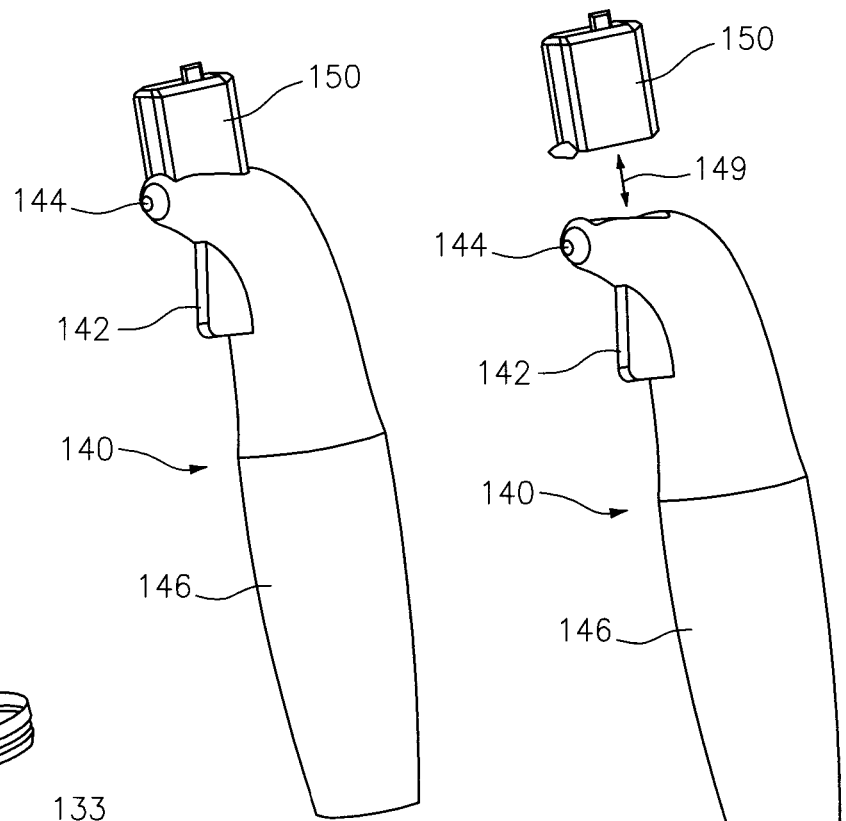
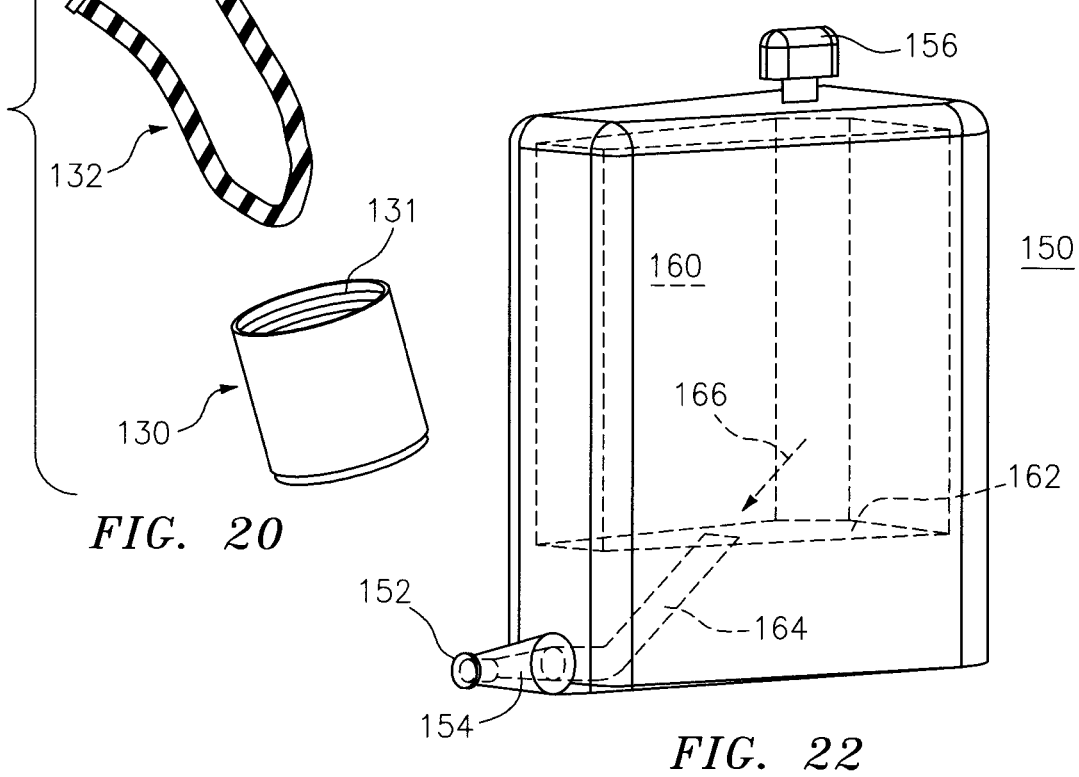
FIG. 20
FIG. 21A
FIG. 21B
FIG. 22

MODIFIABLE OCCLUSIVE SKIN DRESSING

CROSS-REFERENCE TO RELATED APPLICATION

This application is a continuation of U.S. application Ser. No. 14/929,146 filed 30 Oct. 2015, which is a continuation of U.S. Non-Provisional application Ser. No. 13/745,690, filed 18 Jan. 2013, now U.S. Pat. No. 9,173,777 B2 which claims priority to U.S. Provisional Application No. 61/588,121 filed 18 Jan. 2012. The entire contents of each of the above-mentioned applications are incorporated herein by reference.

FIELD OF THE INVENTION

This invention relates to dressings intended to provide a fluid-impervious barrier over skin, and more particularly to dressings suitable for negative pressure wound therapy.

BACKGROUND OF THE INVENTION

Negative pressure wound therapy ("NPWT") is an effective technology for treating open wounds. NPWT devices were originally accepted by the US Food and Drug Administration ("FDA") in 1995, when the FDA approved a 510(K) for the Kinetic Concepts Inc. ("KCI")'s V.A.C.® device. The definition of NPWT devices by the FDA has changed over the years; in general terms, its definition is: a system that is used to apply negative pressure for wound management purposes, including the removal of fluids (i.e., wound exudates, irrigation fluids, and infectious materials). The negative pressure is applied through a porous dressing positioned into or over the wound cavity, depending on wound type and depth, or over a flap or graft; the dressing distributes the pressure while removing fluids from the wound. NWPT systems typically include:

Non-adhesive wound dressing used to fill the wound cavity (e.g., a sterilized medical sponge or gauze; a.k.a., non-adhesive packing materials);

Drainage tube placed adjacent to or into the dressing;

Occlusive transparent film placed over the dressing (and potentially the drainage tube) and adhered to the skin to maintain a seal;

Collection container for drained fluids from the wound; and

Low pressure vacuum source.

NPWT has been approved by the FDA to treat many wound types: chronic, acute, traumatic, sub-acute and dehisced wounds, partial-thickness burns, ulcers (such as diabetic, venous or pressure), surgically closed incisions (a.k.a., closed surgical incisions), flaps and grafts. The prescribed therapy time depends on wound type, wound dimensions, and patient conditions; it typically lasts from four weeks to four months. Disposable dressing components are changed approximately every three days.

Extensive clinical trials have demonstrated the success of negative pressure in healing the approved wound types by applying a controlled negative pressure typically between 20 mmHg and 200 mmHg. Most studies applied a constant vacuum pressure, with 125 mmHg being the most common, although cyclic and intermittent studies are currently underway. Evidence supporting the use of NPWT in the treatment of chronic, non-healing wounds exists primarily in the form of nonrandomized, controlled trials; prospective and retrospective large and small case series; single-center studies; and single case studies, with few randomized, controlled clinical trials. Studies also exist that demonstrate NPWT benefits in healing acute wounds. Additionally, since 2006, benefits of managing surgical incisions post-operatively have been shown with improved clinical outcomes; at least ten studies have been published to date. From these studies, proven medical benefits of NPWT treatment include:

Promotes blood flow (perfusion) at the wound;

Removes interstitial fluid (a.k.a., wound exudates), reduces edema;

Decreases counts of bacteria and infectious materials;

Increases rate of granulation tissue formation, reducing scar tissue formation, increases growth factors and fibroblasts;

Uniformly draws the wound edges together;

Provides a protected healing environment; and

Provides a moist environment.

Although significant clinical evidence exists to support the benefit of NPWT as a safe therapy in healing chronic wounds, it is possible during NPWT to rupture a vein or artery. Usually, a machine safety alarm will signify a fluid leak rate that exceeds the rate that the machine was designed for. This alarmed leak rate typically includes the combination of both air and liquid, and typically has an upper safety limit of the minimum blood flow rate possible out of a wound cavity with an actively bleeding vein or artery. If a vein or artery accidently ruptures, the system must shut down. Therefore, it is very important to have a safety feature that stops blood flow if this occurs, in order not to exsanguinate the patient.

Lina et al. describe in U.S. Pat. No. 7,611,500 and WO1996/005873 an initial apparatus used for NPWT. In practice, the device proved to be effective; however, one major limitation was detected: the high electrical grid power source needed to operate the device limited the mobility of a patient. Therefore, future refinements, such as that described by Hunt et al. in U.S. Pat. No. 6,142,982, incorporated rechargeable batteries for the power source. Batteries increased patient mobility, but time was limited by the life of the batteries between charges. Additionally, battery management became an issue, especially for facilities with a high number of NPWT patients, and electrical grid power was still needed to recharge the batteries.

Eliminating the need for electrical power, via the grid or batteries, would create a more widely applicable, clinically viable therapy. The power requirement variability of a system is dependent on the desired vacuum pressure, rate of wound exudate removal from the wound cavity, and the leak rate of air into the system. As the air leak rate increases, more power is needed to supply a continuous negative pressure at a predetermined value or threshold range at the wound bed. Air leakage into the NPWT system requires the most power of any other component. Air leaks are the obstacle to creating a vacuum system that does not require a continuous external power source or frequent recharging of its internal power storage. Therefore, the feasibility of a mechanical NPWT system is heavily reliant on the seal quality of every interface in the system. The dressing system has been identified as the main source of air leaks in current NPWT systems, particularly at the interfaces between 1) the dressing and the skin and 2) the tube and the dressing. The amount of air leaks into these interfaces determines the time frequency that the pump needs to be recharged and the magnitude of vacuum pressure applied to the wound cavity at a specific time. These two latter characteristics are dependent system parameters.

Few mechanical NPWT systems are currently available, as described by the present inventor in "Development of a simplified Negative Pressure Wound Device" submitted in 2007 for her Master of Science in Mechanical Engineering at the Massachusetts Institute of Technology. Certain lower-pressure, mechanical devices were disclosed later by Hu et al. in U.S. Patent Application No. 2010/0228205. Current mechanical systems typically use sophisticated-material, planar dressings, such as hydrocolloid dressings, to try to solve the air leak problem. However, the inherent geometry mismatch of a planar dressing and the contoured skin surface often leads to air leaks. The mechanical devices therefore are only applicable for select, relatively flat surfaces on the body and, even then, it is difficult to eliminate air leaks entirely.

Non-electrical pumps are at the low end of the spectrum of medical pumps, typically utilizing bladder pumps and capillary action materials. Bladder pumps are used for both extracting and inserting fluids. By their physical characteristics, they are governed by non-linear spring like properties. Currently, bladder pumps are used in wound treatments for drainage purposes, particularly for internal, body cavity drainage. C. R. Bard, Inc. manufacturers many of these non-electrical pumps; one bladder model frequently used to drain internal cavities is commonly referred to as a Jackson Pratt Drain.

There are various limitations to applying NPWT with existing mechanical, bladder pumps. There are no pressure gauges on the pumps and, therefore, the user does not know the initial magnitude of the negative pressure pulled, and cannot monitor the pressure during therapy. Additionally, there are no air leak detection systems for the current pumps, except to visually watch for the expansion of the bladder at a rate higher than expected. If the pump is clear, one can also visually monitor if the expansion rate is due to air leaks or due to drainage fluid.

Capillary action materials are also currently used to treat wounds by providing very low negative pressure treatment, too low to be considered NPWT. This form of treatment is usually found in dressings such as small topical bandages to provide NPWT-like benefits to very small, self-healing wounds, such as blisters and brush burns. Treating a wound with this technology enhances the healing environment. Capillary action materials are filled with small capillaries between the wound and outside environment. A negative pressure is applied by capillary action of fluid flowing from the wound to the outside environment, thereby, removing interstitial fluid. One example of a capillary action material is Johnson & Johnson's First Aid Advanced Care Advanced Healing Adhesive Pads.

Dressing technologies have tried to address the issue of air leaks into NPWT systems. This is important to both electrical and mechanical systems to reduce their necessary power requirements. In mechanical systems, it is necessary for clinically relevant device functionality, such that power input and pump recharge time is reasonable for a caregiver and/or patient to perform. For electrical systems, air leak reduction reduces the number of, if not completely eliminates, false-positive, alarmed emergency system shutdowns. Air leak reduction allows battery designs to last longer on one battery charge and use lower power capacity batteries altogether. Air leak elimination potentially eliminates the need for a continuous power supply, as the vacuum pressure can be maintained in the occlusive environment within a specified threshold, for which the timeframe depends on the pump parameters and exudate removal rate (typically less than 100 mL/day) from the wound.

Currently, most NPWT dressings (the drape component) are thin, planar, tape-like adhesive dressings that must be applied to a contoured area of skin. A backing on the dressing must be removed to expose the adhesive, and then the dressing is applied to the skin. The pre-application handling of the dressings alone introduces a probability for air leaks, as the dressing typically folds onto itself or creases very easily due to its low bending stiffness; many dressings are thinner than a piece of standard paper, and the bending stiffness of a material is proportional to the inverse of its thickness cubed. As a dressing is applied, it must often fold onto itself in order to accommodate for a geometrical mismatch between the planar dressing and the contours of the body surrounding the wound to be treated. This creates creases, also referred to herein as wrinkles, in the dressing that have a high potential for causing air leaks into the NPWT system.

Adding to the geometrical mismatch, the dressings often become less adhesive due to the introduction of foreign materials onto the adhesive before dressing application. This is most common and almost unavoidable at the edges of the dressing due to handling by the caregiver. At times, the caregiver's hands introduce enough foreign particles onto the adhesive to forbid further adhesion of that area of the dressing. In the U.S., this often happens when a caregiver uses powdered gloves. This is a critical issue as the edges of the dressing are an area where leak propagation from the edge of the dressing to the wound cavity is potentially very high, based on the theory of interface fracture mechanics.

For the electrical NPWT systems, a thin plastic, adhesive backed dressing is typically used. Electrical NPWT dressing systems have not readily addressed the air leak issues listed above that form at the dressing-to-skin interface. Instead, dressing iterations have focused on air leaks at the tube-to-dressing interface. When NPWT was first introduced into the market, the drainage tube was inserted into the wound cavity through the edge of the dressing. This introduced a high potential for air leaks, which often alarmed the shut-off system. Caregivers began to solve this problem by raising the tube from the skin surface at the dressing edge, and pinching the dressing under the tube before the dressing contacts the skin. This caused the dressing to adhere to itself in an upside-down "T" pattern onto the skin.

Eventually, some of the NPWT dressing, commercial designs incorporated their own solutions to the high air leak rate at the tubing interface. Out of these solutions, the T.R.A.C. Pad by KCI was highly effective, which is driving the current design trends. The T.R.A.C. Pad prefabricates the drainage tube to a semi-rigid, tubing connector, which is then attached to a small, circular, planar adhesive dressing (a.k.a., drape). All of these connections are made air-tight during its manufacture. The tubing does not travel beyond the plane of the adhesive dressing, and therefore its opening remains at the skin surface. When the T.R.A.C. Pad is used, the standard dressing is initially applied to the wound, without a tubing connection. Then, a small incision is made in the dressing, over the wound cavity; this hole may also be prefabricated into the drape component of the dressing during its manufacture. The film backing of the circular adhesive component is removed from the Pad, and the tube opening is centered over the incision. Since the adhesive surface of the Pad is small, it is easier to handle than the procedure of tunneling the tube into the initial dressing. Although the Pad does not guarantee elimination of air leaks at the tube-to-dressing interface, it highly reduces the probable amount of air leaks into the dressing, based on its ergonomic design and small profile. A minimal amount of air leaks is almost unavoidable for all applications with planar adhesive components, due to the geometrical mismatch and user handling that still remain.

Many efforts have been made in order to overcome the identified barriers of low end, mechanical pumps for application in NPWT. Most of the focus has been on reducing air leaks and creating more predictable vacuum sources. New materials used in NPWT dressings have been the main driver in reducing the air leak rate into the system at the dressing-skin interface. These materials are often not new to wound dressings; however, they are new to NPWT. Pump design has been the focus of creating more predictable vacuum sources; mechanical components, such as linear or constant force springs, are often introduced into the system and maintain a more predictable behavior throughout therapy.

Only one mechanical NPWT system is on the market today, but is not widely used: SNaP® Wound Care System by Spiracur (Sunnyvale, Calif.). The SNaP® Wound Care System uses a hydrocolloid dressing with specific mechanical connectors from the tube to the dressing, in order to accommodate for air leaks; the provided hydrocolloid dressing is relatively small in size. Hydrocolloids are used in many wound-dressing systems, and are a common trend in the NPWT market. They are stiffer and thicker than most common, adhesive, planar, NPWT specific dressings. This causes the dressing to fold onto itself less during its handling and application. However, it cannot accommodate for geometrical mismatch without creases, especially as the dressing surface area increases. Since the dressing is stiffer and thicker, these creases are difficult to seal in an air-tight manner, due to its increased bending stiffness. Therefore, hydrocolloids are often only applicable to smaller wounds. Much effort is currently being taken to make them thinner, in order to increase their applicable surface area and accommodate more for contours, such as the Replicare Thin Hydrocolloid Dressing by Smith and Nephew. Hydrocolloids rely on their extremely sticky adhesive properties to account for increased skin adhesion and reduced air leaks. If they come in contact with wound exudate, the polymers in the hydrocolloid swell with water until saturation, forming a gel, which is held solid in its adhesive matrix structure.

In the SNaP® Wound Care System, the hydrocolloid dressings are connected to the tubing with a mechanical connector component, similar to the T.R.A.C. Pad, KCI. The SNaP® Wound Care System eliminates any potential air leaks from this mechanical connector by prefabricating it to the center of the entire dressing during manufacture. The prefabrication eliminates any potential air leaks at the tube-to-dressing interface due to user interface and geometrical mismatch, but it is not capable of being moved on the dressing surface. Therefore, it may need to be placed on an inconvenient area of the wound, such as a location that is uncomfortable for the patient. Additionally, the tube runs parallel to the plane of the drape; the direction of the tube along the plane of the drape is fixed. Since the dressings are not typically round, the tube path may be required to travel in an undesirable path, in order to cover the wound area with the preset shape of the drape.

For its vacuum source, the SNaP® Wound Care System uses a complex system, driven by constant force springs. Therefore, as the pump expands, mainly due to air leaks and potentially exudate removal, the pressure remains relatively constant for the length of the pressure application. This system is expensive and highly technical when compared to the non-electrical pumps at the low end of the medical pump spectrum (e.g., bladder pumps); however, it is the first commercial mechanical NPWT pump, which has been proven to be a potential NPWT pump design. Since air leaks into the dressing system remain highly probable, depending on wound location and caregiver experience, the successful application of the SNaP® Wound Care System is limited in practice.

SUMMARY

Occlusive skin dressings according to the present invention preferably provide one or more of the following advantages:
a conformable dressing system that can be altered if desired and applied to substantially all areas of the skin surface;
a dressing system that is ergonomic;
dressings that are easy to obtain and re-obtain by the user, through conveniences in storage;
dressings, pumps, systems, and methods to administer NPWT without the need for electrical power;
minimizing the amount of air leaks into the NPWT system;
detecting air leaks into the NPWT system;
compatible with light-weight, easily transportable and low cost pumps; and
mechanical methods to minimize the possibility of exsanguinating the patient.

Occlusive dressings according to the present invention overcome the aforementioned drawbacks by being truly air-tight. One principal application of this technology is to facilitate administration of mechanical NPWT. A liquid component is applied at the dressing-to-skin interface in order to create a substantially air-tight seal preferably for at least 48 hours, more preferably for at least 72 hours. Preferably the same or different liquid component is applied at the tube-to-dressing interface in order to create a similar air-tight seal. In some embodiments, the liquid components may be made of rubber polymers applied by touch, by squeezing a dispenser, or by spraying the polymers with an atomization process.

This invention features a kit suitable for occlusively sealing a wound penetrating the skin of a patient, including a drape formed as a thin sheet of an organic, preferably elastomeric material, substantially impervious to fluid transfer of air and bodily fluids, having first and second surfaces. A biocompatible adhesive is at least one of (1) disposed on at least the first surface of the drape and (2) capable of contacting at least a portion of at least the first surface of the drape. When the kit includes the biocompatible adhesive disposed on at least a portion of the first surface of the drape, the kit further includes at least a first removable liner sheet covering the first surface of the drape. In some embodiments, a second removable liner sheet covers the second surface of the drape, especially when adhesive is also disposed on the second surface of the drape. The kit further includes at least one container of at least one sealant component that is capable of being delivered as a sealant in a liquid state at pre-selected ambient conditions, the sealant as delivered being at least partially cross-linked at least after one of drying and curing, and which is capable of at least one of drying and curing within thirty minutes, preferably within twenty minutes and, more preferably, within ten minutes, after application of the sealant as a layer to the edges of the drape after the drape is applied to the skin surrounding the wound.

In some embodiments, the drape and the sealant after one of drying and curing are elastomeric. In a number of embodiments, the drape and the sealant are derived from substantially the same material, such as a type of a latex compound or a type of silicone compound. In certain embodiments, the adhesive is a silicone-based adhesive and is disposed on at least a majority of each of the first and second surfaces of the drape as a solid coating or in a pattern such as a grid or concentric circles. At least one container of a sealant component enables manual application of the sealant in some embodiments, such as by squeezing the container and, in other embodiments, at least one container is a removable vial or cartridge insertable into a dispensing apparatus or other applicator. In a number of embodiments, the kit further includes a flexible tube having a first end and a second end connectable to a source of negative pressure such as a bellows, especially a novel bellows which unrolls, or other mechanical vacuum source. Preferably, the kit further includes a flange having at least one of (1) a central passage through which the first end of the tube is insertable and (2) a central passage communicating with a connector capable of mating with the first end of the tube. In one embodiment, the first end of the tube includes a feature such as a spiral cut to resist blockage of the tube. In some embodiments, the kit includes at least one non-stick handling component. In a number of embodiments, the kit further includes at least one wound packing material.

This invention may also be expressed as a method of constructing an occlusive dressing over a wound penetrating the skin of a patient by selecting a drape formed as a thin sheet of an elastomeric material, substantially impervious to fluid transfer, and having first and second surfaces. A biocompatible adhesive is selected that is at least one of (1) disposed on at least the first surface of the drape, preferably with a first removable liner sheet covering the first surface of the drape and (2) applied to at least one of (i) the skin of the patient surrounding the wound and (ii) at least a portion of at least the first surface of the drape. Optionally, a second removable liner sheet covers the second surface of the drape. The method includes removing the first removable liner, if present, and placing the drape onto the skin surrounding the wound, removing the second removable liner if present, and applying a sealant that is in a liquid state as applied, the sealant being at least partially cross-linked at least after one of drying and curing, on at least the edges of the drape and on the skin adjacent to the drape in one or more layers. The method further includes at least one of drying and curing the sealant within thirty minutes, preferably within twenty minutes, after application of the sealant to the edges of the drape in at least one layer.

In certain embodiments, the adhesive is disposed on at least a majority of each of the first and second surfaces of the drape, and/or the method includes pressing on the second surface of the drape in the vicinity of any wrinkles in the drape, preferably before sealant is applied in that vicinity. In some embodiments, a flexible tube is selected having a first end and a second end connectable to a source of negative pressure such as a bellows or other mechanical vacuum source. Preferably, the first end of the tube (1) is inserted through a central passage of a flange secured to the drape or (2) is mated with a connector on a flange having a central passage communicating with the connector. In one embodiment, the first end of the tube includes a feature such as a spiral cut to resist blockage of the tube. In some embodiments, the wound is packed with gauze or other fluid-pervious material prior to placing the drape on the skin.

This invention may be further expressed as a method of constructing an occlusive dressing over a wound, penetrating the skin of a patient, by at least one of (1) packing the wound with a fluid-pervious material and (2) covering at least a portion of the wound with a protective material. The method further includes applying, such as by spraying, an elastomeric material that is in a liquid state, and is at least partially cross-linked at least after one of drying and curing, over the packed material and onto skin surrounding the wound to create an occlusive drape as a thin sheet substantially impervious to fluid transfer, having a first, inner surface and a second, outer surface. The method includes at least one of drying and curing the elastomeric material within thirty minutes after application of the elastomeric material as a layer.

BRIEF DESCRIPTION OF THE DRAWINGS

In what follows, preferred embodiments of the invention are explained in more detail with reference to the drawings, in which:

FIG. 1 is a schematic expanded perspective view of a drape, flange and tube with first and second liners prior to application of a liquid sealant according to the present invention;

FIGS. 2 and 3 illustrate a novel first end of the tube of FIG. 1 being inserted through the novel, preferably symmetrical flange;

FIG. 20 is a schematic expanded view of a vial of sealant with a non-stick finger protector optionally positionable within the vial for storage and transportation;

FIGS. 21A and 21B show a dispensing apparatus with removable cartridge of liquid sealant;

FIG. 22 is an enlarged perspective view of the cartridge of FIGS. 21A and 21B;

DETAILED DESCRIPTION

Figure 4:
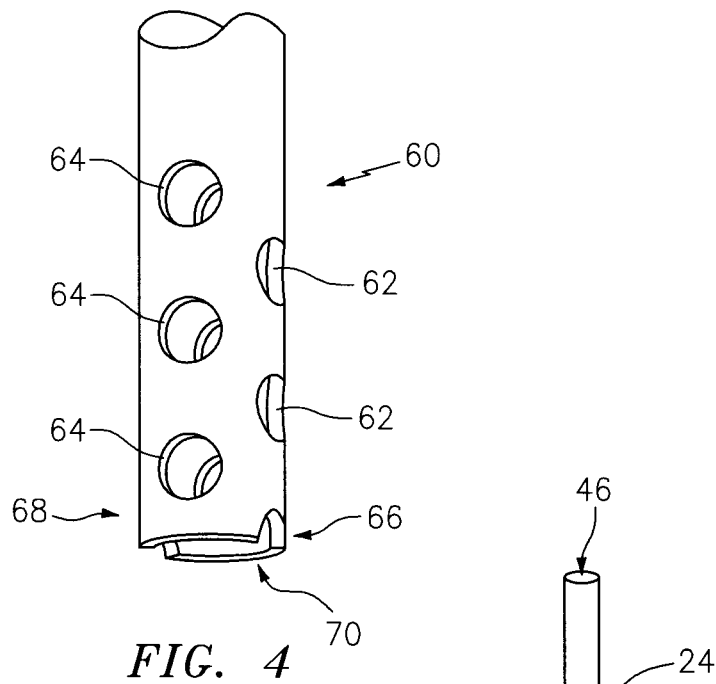
FIG. 4 is a schematic perspective view of an alternative novel first end of a tube.

This invention may be accomplished by a kit, dressing system or method utilizing a drape formed as a thin sheet of an organic, preferably elastomeric material, substantially impervious to fluid transfer of air and bodily fluids for preferably at least 48 hours, more preferably at least 72 hours, having first and second surfaces. Preferably, a biocompatible adhesive is disposed on, applied to or contacted with, at least the first surface of the drape. In a number of constructions, a first removable liner sheet covers the first surface of the drape and, optionally, a second removable liner sheet covers the second surface of the drape. The invention further utilizes a container of at least one sealant component that is capable of being delivered as a sealant in a liquid state at pre-selected ambient conditions, the sealant as delivered being at least partially cross-linked at least after one of drying and curing, and which is capable of at least one of drying and curing within thirty minutes, preferably within twenty minutes and, more preferably, within ten minutes after application of the sealant as a layer to the edges of the drape after the drape is applied to the skin surrounding the wound.

The occlusive dressings presently disclosed address the power/mobility and air leak issues by eliminating the need for an electrical power source and by maintaining reliably air-tight interfaces, particularly at 1) the dressing and the skin and 2) the tube and the dressing. The disclosed dressing systems and their connection methods allow for reliable, mechanical NPWT systems. Not only does this eliminate patient mobility and battery management issues, but it also allows NPWT to be administered in austere environments, where electricity is often scarce and harsh environments require robust products. Multiple disclosed embodiments support an inexpensive, robust therapy method for global application. Additionally, dressings according to the present invention are MRI-compatible.

In order to obtain an air-tight skin dressing, the present occlusive dressings use a liquid sealant. This liquid sealant may dry and cure fast, even immediately or effectively immediately, upon application to the skin or other dressing components, into a continuous, occlusive film or sheet of material. The drying and curing processes may occur simultaneously, may be driven by evaporation, may require a curing agent and/or accelerator, and/or may be enhanced or controlled with a curing agent and/or accelerator. Any extra additives (e.g., curing agents and accelerators) may be added just before, during, and/or after the sealant application process, depending on its chemical reaction with the sealant and its rate.

The liquid sealant bonds to the component(s) that it is meant to seal. The ability of Van der Waals forces to provide the bond strength without an added adhesive is based on the material and its thickness. Theoretically, the debond toughness (strength of the bond) must be greater than the debonding energy, and the debonding energy is proportional to: the thickness of the material, the strain in the material squared, and the elastic modulus of the material. Specifically (on a first order basis; as its basis is a small strain analysis), the bond strength of a thin film must abide by Equation 1, where $\Gamma$ is the debond toughness, $\varsigma$ is the debonding energy, $\Omega$ is a dimensionless prefactor, h is the thickness of the film, $\varepsilon_T$ is the strain in tension, and $E_f$ is the elastic modulus of the film, in order to maintain adhesion to the skin in tension:

$$\Gamma > \varsigma = \Omega h \varepsilon_T^2 E_f \qquad (1)$$

Therefore, a highly elastic, thin film presents the ideal material properties for reduced, required adhesion strength, increasing the functional applicability of the Van der Waals forces.

An additional adhesive, such as a silicone-based, latex-based, or acrylic-based glue, having one or more components, might be employed to produce the desired bond strength (for example, Liqui-Tape Silicone Adhesive, Waterproof by Walker Tape Co., West Jordan, Utah). This adhesive can be applied under the liquid sealant or chemically mixed with the liquid sealant prior to its application, depending on its chemical make-up and final mixing properties. When applied under the sealant, the adhesive may need to become tacky (a.k.a., applied set time) prior to sealant overlay. A fast-setting, two-part sealant that is mixed prior to use may be useful in some circumstances, such as Skin Tite® silicone available from Smooth On, Easton, Pa., which is ACMI Certified Safe and may be used by itself or mixed with a thickener, such as Thi-vex® thickener, also available from Smooth On. A polymer sealant, or other material with the ability to bond into a continuous occlusive sheet, with adhesive-like properties due to high Van der Waals forces may be desirable, where no additional adhesive is needed.

Rubber polymers, such as latex, synthetic rubber, and hypoallergenic latex, are examples of polymers with desired properties for both the dressing-to-skin and tube-to-dressing interfaces. For example, Deviant Liquid Latex from Deviant, a subsidiary of Envision Design, San Jose, Calif. and Liquid Latex Fashions Body Paint from Liquid Latex Fashions, Warrington, Pa. were both demonstrated to seal the dressing at both dressing interfaces. The drying and curing time for the latex was significantly reduced by applying the liquid to the skin with an atomization process, which is further disclosed in the sections below, by adding alcohol, which helps to absorb the water that evaporates from the latex, and/or by flowing a gas across the sealant for convection drying. For most applications, the curing/drying time was lowered to immediately (at most 1 minute) from the 5-10 minutes previously stated by Deviant at www.liquidlatex.net.

Examples of suitable latex materials include Vytex Natural Rubber Latex (NRL), a brand of natural rubber latex produced and marketed by Vystar Corporation, Duluth, Ga. Vytex is manufactured by Revertex Malaysia and distributed by Centrotrade Minerals and Metals, Inc. Protein test results show that Vytex NRL typically has 90% fewer antigenic proteins than Hevea natural rubber latex. Therefore, Vytex causes less exposure and developed latex sensitivities. The Vytex has two products with different levels of ammonia; ammonia is a stabilizer and preservative, and both functionally are feasible for the NPWT liquid sealant and drape components, although alternative stabilizers to ammonia may irritate the skin less. Liquid latex for body painting typically contains ammonia, which is what has been applied to patients during field studies with no irritations. Vytex NRL, low ammonia compound, has provided functional, occlusive drape and sealant components on clean, unwounded skin in a lab setting.

Yulex Corporation, Phoenix, Ariz. creates hypoallergenic latex from guayule (*Parthenium argentatum*). Yulex's guayule biorubber emulsions and solids have none of the sensitizing antigenic proteins found in traditional Hevea latex and is considered a safe alternative for people with Type I allergies. Yulex's biorubber emulsions are registered with the Personal Care Product Council and its INCI name is *Parthenium argentatum* Bark Extract. This is a presently preferred material for the NPWT dressing and sealant, in order to provide a non-allergenic material option. Yulex presently has ammonia and ammonia-free options.

Synthetic materials such as nitrile rubber and neoprene are alternatives to natural rubber that do not have allergy-provoking proteins, but can also generally have poor elasticity with higher risk of break rates and viral penetration rates. Therefore, they are less ideal for many of the dressing applications according to the present invention, but may be suitable in some circumstances, particularly for the drape for which curing on the skin and drying time are not issues. Other multi-part materials, such as Room Temperature Vulcanizing silicones and certain polyurethanes which are two-part materials with base and curative components, may be acceptable in some applications.

Extremely low stiffness, which is achievable with many rubber-type materials, increases its bonding ability through Van der Waals forces alone. The high elasticity capable of being achieved using rubber polymers accommodates for the high levels of tensional strain reached at the skin surface during large deformation body movements. Additionally, the material properties of rubber polymers may also accommodate for the tendency to buckle when compressive strains are applied, depending on any initial interface crack sizes and adhesion strength. A desirable sealant accommodates for the large variability over time and surface area of the skin surface strains experienced during large deformation human motions; in the literature, the maximum large deformation strain is indicated to be approximately 0.45 in tension and 0.3 in compression. As rubber mechanical properties are sufficient to achieve structural integrity, the Van der Waals adhesive properties determine the applicable occlusive sealants, and depending on the polymer, an additional adhesive may be necessary.

The liquid sealant should have viscosity and curing properties, preferably including minimal shrinkage, that enable it to conform to all contact surfaces during the application and curing processes, such that no air leak channels at the interface are present after its application. At the dressing-to-skin interface, the sealant should conform to the folds and creases in the skin that are often bridged when applying a standard, planar wound dressing. These types of bridged cracks at all component interfaces are often a significant source of air leaks into the system without a liquid sealant. Once a crack exists, crack propagation occurs in tension and compression with reduced, applied strains, so air leak channels can form overtime with reduced strain magnitudes. Therefore, eliminating any initial cracks at all of the interfaces is desirable. At the dressing-to-skin interface, structures, such as hair, often create opportunities for crack propagation and air leaks into a wound dressing, and therefore, hair is often shaved before dressing applications. The need to shave the hair from an infectious standpoint is not desirable, as the shaving process creates trauma at the hair follicles and increases the risk of infection. With a liquid sealant, these structures can be completely enclosed in the air-tight sealant, and therefore, are not a source of crack propagation under the sealant and do not typically require removal prior to the sealant application, as cracks at the dressing edges are most critical to seal, in order to resist crack propagation due to tension. In some constructions, adhesive on the first surface of the drape is sufficiently thick and/or flowable to seal around hairs and skin crevices and to minimize crack propagation.

The sealant thickness, number of components, wound location, and sealant viscosity determines the optimal sealant application method(s). The liquid sealant may have a very high to low viscosity, as long as it can completely wet the contact surfaces. If mechanically applied (e.g., brush or "painting" application, roller application, sponge/dabbing application, squeegee or other squeeze-type application, application by-hand (i.e., finger) with or without a non-stick cover, etc.), a viscosity that avoids run-off due to gravity is preferable in order for the sealant to be ergonomically applicable to any wound location. This leads to higher viscosities and is limited at the low viscosity range. Painting is not the preferred application method; when painting the sealant, it is difficult to achieve a constant thickness. If the thickness varies significantly over its surface area, the mechanical properties and debonding energy will also vary significantly, which may cause occlusive dressing failure. Painting also has other drawbacks, as it is easy to trap air bubbles in the sealant, which are a source of cracks for crack propagation. Also, it is difficult to produce and maintain a very thin coat, which significantly increases the necessary Van der Waals bonding strength; it increases the stiffness of the final dressing and decreases its ability to conform to large tissue strains.

Spraying is a preferred method of applying the sealant. Two types of spraying procedures are possible: 1) an aerosol process which propels the liquid sealant with a pressurized liquid or gas propellant that forces the liquid sealant through an atomizing nozzle, and 2) a shearing process which shears the liquid sealant with a pressurized gas or liquid causing atomization. When atomized, the layer of sealant material can be made thin enough that run-off is less of an issue, and therefore a range of lower viscosities can be used for their desired wetting characteristics. Additionally and in combination, the small atomized particles fill in the structures on the skin for wetting purposes. The spraying technique is limited at the high viscosity range, as too high of a viscosity sealant will not be capable of being sprayed with reasonable pressures and velocities for application in the clinical setting onto skin. However, this is not seen as a negative aspect since liquids with very high viscosities often do not properly wet the complex contours of the skin surface.

The shearing process may be preferred over the aerosol process. One reason for this preference is that nozzles clog easily with long polymer chains, unless the liquid can be further thinned. Using the shearing process, the shearing fluid and sealant fluid may be kept separate until they are both external to the nozzle head. Therefore, internal clogging of the nozzle does not occur when properly designed, including a fluid filter (if necessary) and the proper nozzle orifice size. Gas is the preferred shearing fluid, as it does not add additional liquid to the system for drying purposes, it is easy to propel since it can be compressed to high pressure levels, and it helps to dry the sealant when spraying it onto the skin. Higher viscosities and materials with long polymer chains are capable of being sprayed by the shearing method rather than the propellant method, although the viscosities and chemical chains that can be accommodated with the propellant method can be increased with complex nozzle design.

Additives such as curing agents, accelerators, convection drying agents, and adhesives may be applied via separate application methods, if they are not mixed with the sealant prior to application. Their application method may be via painting or spraying. The application of these additive components and the sealant may occur in a multi-step process. They may be stored and applied from separate containers with the same or different application methods in series or in parallel. However, they may also be applied in parallel or series from the same containing body. One example is a parallel spraying process, for which three ports exist: the sealant port, the shearing fluid port, and an accelerator port; these three components can combine during the atomization process in the spray nozzle where the three ports may interact. Another example is a spray apparatus that allows the amount of sealant (and potential accelerator) to be controlled, such that it may be shut-off; the shearing gas then becomes a convective drying gas.

Various polymers with rubber-like properties were determined to have the desired sealant properties. Additionally, a preferred sealant cures immediately or within a few seconds after surface contact. With these characteristics, the polymer tends to have long and heavy polymer chains, and therefore, requires the higher atomizing forces capable with the shearing process. As gas is used to atomize the polymer, there is a desirable range of gas pressure, velocity, and volume flow combinations that are required for the desired, continuous-film outcome. Filtered air, pure oxygen, and carbon dioxide are examples of applicable shearing gases that can be readily used, and are often available in the clinical setting at the desired pressures and volume flow rates. They are also readily available outside the clinical setting. Using these gases, the necessary, shearing atomization process is capable of being designed into a miniaturized handheld device. This process and design is similar to the consumer use of the aerosol embodiment commonly found in consumer products and is further disclosed in the Dressing Application Methods section.

The thickness of a desired seal embodiment can be built-up in a successive layered, lamination process. A material that has a strong affinity for itself with either strong Van der Waals forces or chemical bonds that form between its layers, such that the final material behaves as a continuous one-layer sealant is desirable. The desired thickness is the minimal thickness needed for strength and to achieve the desired occlusive properties, which is material dependent. This thickness is often thinner than the thickness that can be reliably and uniformly achieved through a painting process, and therefore a spraying process is often preferred. The atomization process provides a method to achieve the thinnest functional sealant thickness.

Occlusive dressings are beneficial beyond NPWT and in combination with advanced NPWT features. Some proven benefits of occlusive properties are highlighted here. The occlusive characteristic may enhance the penetration and absorption of topically applied medications, such as ointments, powders and creams, which can be beneficial in combination with standard wound dressings and with therapies, such as NPWT. The V.A.C. Instill Therapy Unit (KCI) was meant to combine instillation therapy with NPWT. Instillation, as defined by the V.A.C. Instill documentation, includes both: 1) the introduction and removal of topical solutions in liquid form and 2) the ability to flush out and clean a wound through a rigorous irrigation technique. The main caregiver complaint about this and other instillation-purposed dressings is that they often leak liquid during the instillation process, especially during a rigorous irrigation procedure, which further induces air leaks during continued therapy. The occlusive seal and dressings disclosed in this disclosure would solve any leak issues that arise. Often the irrigation process introduces leaks by propagating cracks in the dressing; by eliminating these cracks, the sealant and dressing techniques in this disclosure significantly reduce the potential for leaks and leak formation during instillation. The port(s) needed for instillation fluid insertion and removal can be directly connected to the disclosed occlusive dressing embodiments with the same tube-to-dressing connection methods that are disclosed in the Tube-to-Dressing Interface section in this disclosure.

Although the presently disclosed occlusive dressings were developed with NPWT system in mind, they can be used for any application for which an occlusive (a.k.a., air tight and water tight), air tight, or water tight seal to the skin is desirable. Therefore, they are applicable in multiple fields beyond NPWT, and more generally in the field of skin sealants and their methods. Truly occlusive dressings create a control volume over the area of tissue that they are applied, which is a desirable feature for multiple applications, many which are disclosed in this application document.

The occlusive dressings discussed in this disclosure are the first skin dressings to provide a control volume, as no other dressing to-date is proven to be (reliably) truly occlusive. This would benefit the enhancement of advanced healing therapies that are sensitive to any variation in the environment, such as stem cell based therapies, for which complete control of the environment is necessary to achieve deterministic results. If a specific air leak is desirable, its rate can be precisely controlled into the control volume through precision valves. Currently, there is no accurate predetermination for the air leak rate into any wound dressing, especially since most dressing air leaks have variability over time and with body movement. Furthermore, truly occlusive dressings may be used in in vivo acute toxicity tests of dermal irritation and sensitization. The test animal is shaved and the test material is applied to the skin and wrapped in an occlusive material. The skin is then exposed after 23 hours and an assessment for redness and edema is made; this assessment is repeated 48 hours later.

FIG. 1 is a schematic expanded perspective view of a dressing assembly 20 including a drape 22, a novel flange 26 and a tube 24 with first and second protective liners 28 and 30 prior to application of a liquid sealant according to the present invention. Drape 22 and second liner 30 define holes 32 and 34, respectively, through which tube 24 is insertable.

FIGS. 2 and 3 illustrate a novel first end 40 of the tube 24 of FIG. 1 being inserted through the novel symmetrical flange 26 to form a tube assembly 27, FIG. 3. First end 40, also referred to as distal end 40, includes a spiral extension 42 which, in one construction, is formed by making a helical cut into the distal end of tube 24. In other constructions, a separate component having a helical shape or other geometric shape is attached to serve as a deterrent to clogging of distal end 40. Spiral extension 42 minimizes possible blockage of lumen 46 through tube 24. Another anti-blockage construction is illustrated in FIG. 4 with a tube distal end 60 defining perforations 62 and 64, notches 66 and 68, and a blunt tip 70. Perforations 62 and 64 can be formed as diamond-shaped cut-outs, circular holes, or other geometries. A notch 44, FIG. 2, is also created in this construction to further minimize the possibility for lumen 46 through tube 24 to become obstructed, as described in more detail below.

Figure 5A:
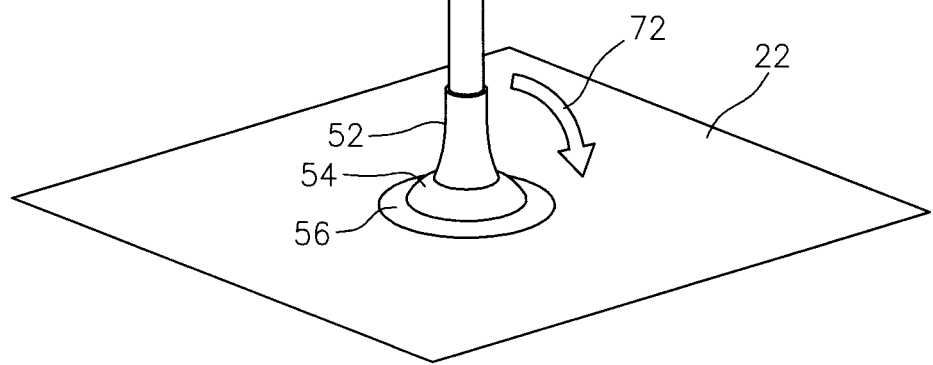
FIGS. 5A and 5B illustrate repositioning of the upright tube into a desired side orientation.
Figure 5B:
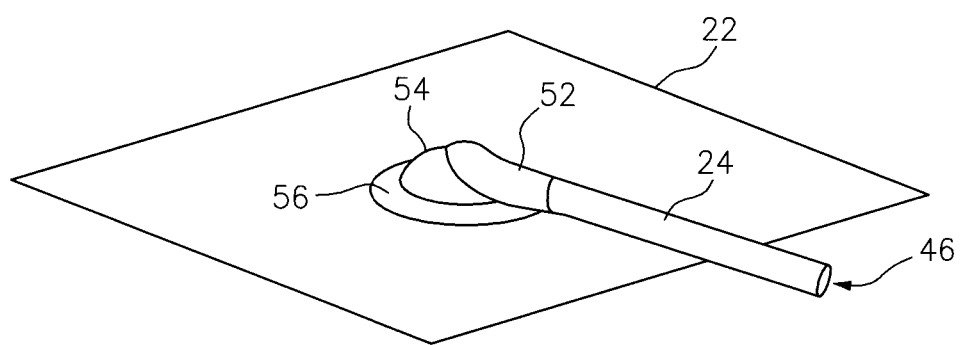
Figure 43:
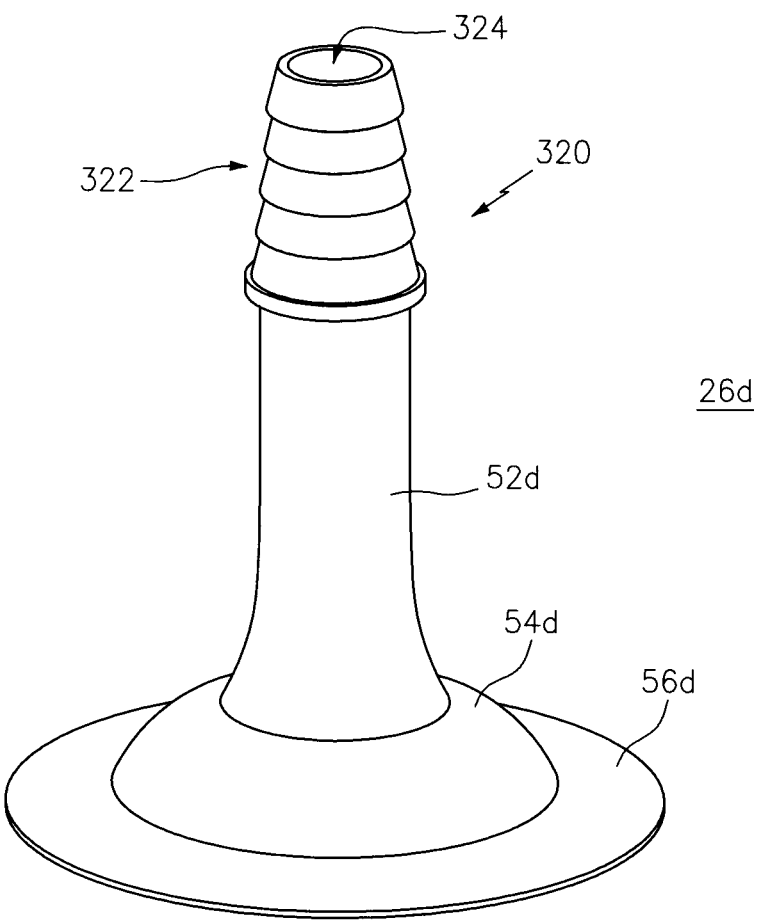
FIG. 43 is a schematic perspective view of a novel flange according to the present invention with integral connector.

Arrow 48, FIG. 2, represents distal end 40 being inserted through passage 50 in flange 26 defined by a sleeve region 52, a rotation region 54, and an adhesion region 56 having an outer edge 57. Sleeve region 52 is adhered to tube 24, as described in more detail below, at a final location such as shown in FIG. 3. In another construction, sleeve region 52 is attached, via adhesion, welding or other air-tight connection process, to a short piece of tube with a connector that connects to a longer piece of tubing. In yet another construction, the flange includes an integral connector capable of mating with flexible tubing such as shown in FIG. 43. Rotation region 54 serves as a flexible ball joint in this construction. As depicted in FIGS. 5A and 5B, tube 24 can be manipulated in the direction of arrow 72, FIG. 5A, to a desired side orientation as shown in FIG. 5B. Lumen 46 through tube 24 remains open in some constructions because distal end 40 extends beyond adhesion region 56, with notch 44 preferably below sleeve region 52 but above adhesion region 56, so that rotation region 54 does not collapse onto itself. In other constructions, the flange is sufficiently short and wide to minimize the possibility of pinching closed. Sleeve region 52 is sealed in an air-tight, fluid-impervious manner in some constructions by first applying a silicone adhesive, such as Liqui-Tape adhesive from Walker Tape Company as mentioned above, to the portion of the outer surface of tube 24 which will be brought in contact with sleeve region 52 during assembly. A liquid sealant can be applied to the junction of tube 24 and flange sleeve region 52 to further occlude possible fluid escape at that junction.

In some constructions, flange 26 is manufactured directly onto tube 24, via a dipping, molding or spraying process. In constructions where flange 26 is constructed entirely from, or coated with, a material that has an affinity for itself, sleeve region 52 may self-adhere to rotation region 54 and adhesion region 56, to the extent that region 56 is exposed, when folded against itself as shown in FIG. 5B. Where the material forming the exterior of flange 26 has an affinity for the material of drape 22, especially for materials containing latex compounds, the exterior of sleeve region 52 will also adhere to drape 22 at least to some extent; latex-type material applied to the surface of tube 24 will further enhance this adhesion. Fixing the tube 24 into a fixed orientation such as shown in FIG. 5B may be especially beneficial for bed-ridden or less mobile patients so that the tube can be positioned to avoid the patient lying on the tubing for long periods of time or to avoid compromised areas around the wound. In other circumstances where the tube remains movable, it can be easily repositioned because rotation region 54 remains flexible and the tube can be monitored and moved frequently to assure that tissue is not degraded from lying on the tube in one position for an extended period. Especially for active patients, the tube 24 can be periodically re-positioned by the patient or by a healthcare professional.

Figure 6:
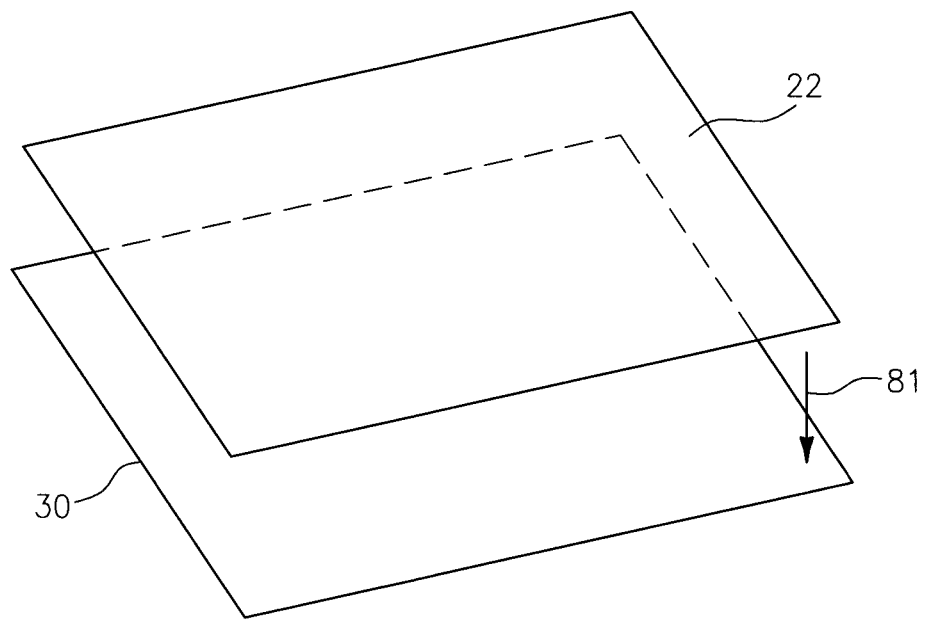
FIGS. 6 and 7 show a drape being covered by an upper liner to manufacture a dressing according to the present invention.
Figure 7:
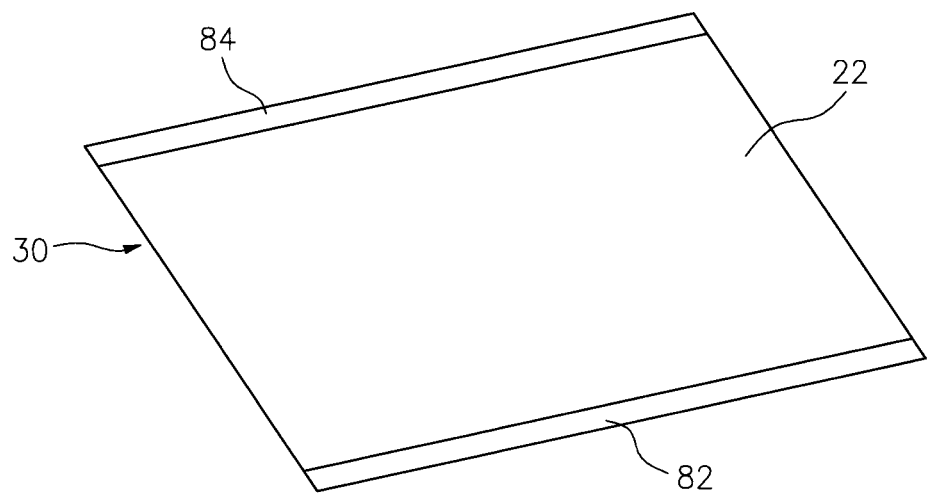

FIGS. 6 and 7 show a drape 22 being covered by an upper liner 30 to manufacture a dressing according to the present invention. Preferably, drape 22 has a thickness ranging from 2 microns to 0.4 mm, especially in portions which will be applied to skin; a greater thickness in the center portion to be located over a wound is less critical for occlusivity. In some constructions, adhesive is pre-applied on the upward-facing surface shown in FIGS. 6 and 7, which will be placed in contact with skin during use; in other constructions, adhesive is also placed on the opposite side of drape 22, to be covered by liner 30, as indicated by arrow 81 in FIG. 6, for storage and handling. The adhesive is applied as a uniform coating in some constructions and, in other constructions, as concentric circles or other non-uniform pattern. Preferably, liner 30 has extensions 82 and 84 which extend beyond the drape 22 to facilitate handling of the dressing without touching any adhesive, and to enable easy removal of the liner 30 from the drape 22 after placement on a patient.

Figure 8:
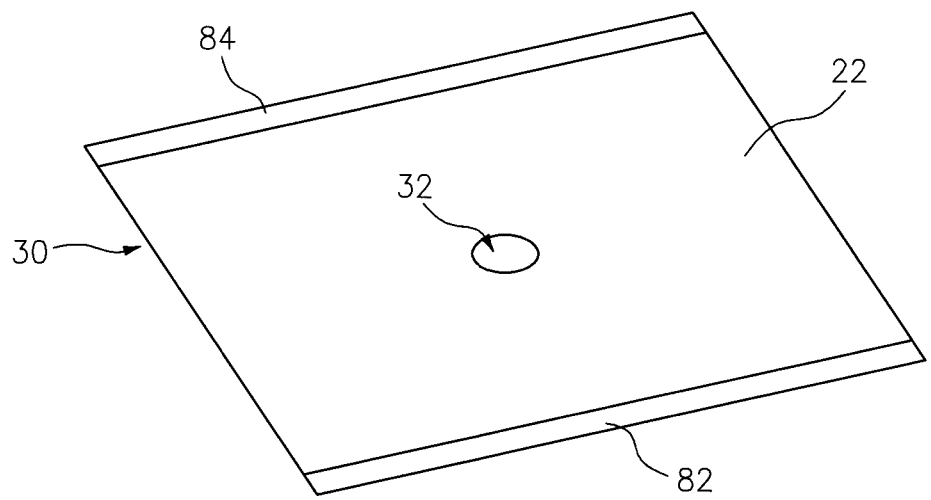
FIG. 8 shows a hole punched in the dressing of FIG. 7.

FIG. 8 shows a hole 32 punched in both layers of the dressing of FIG. 7. Hole 34, FIG. 1, is not visible in FIG. 8.

Figure 9:
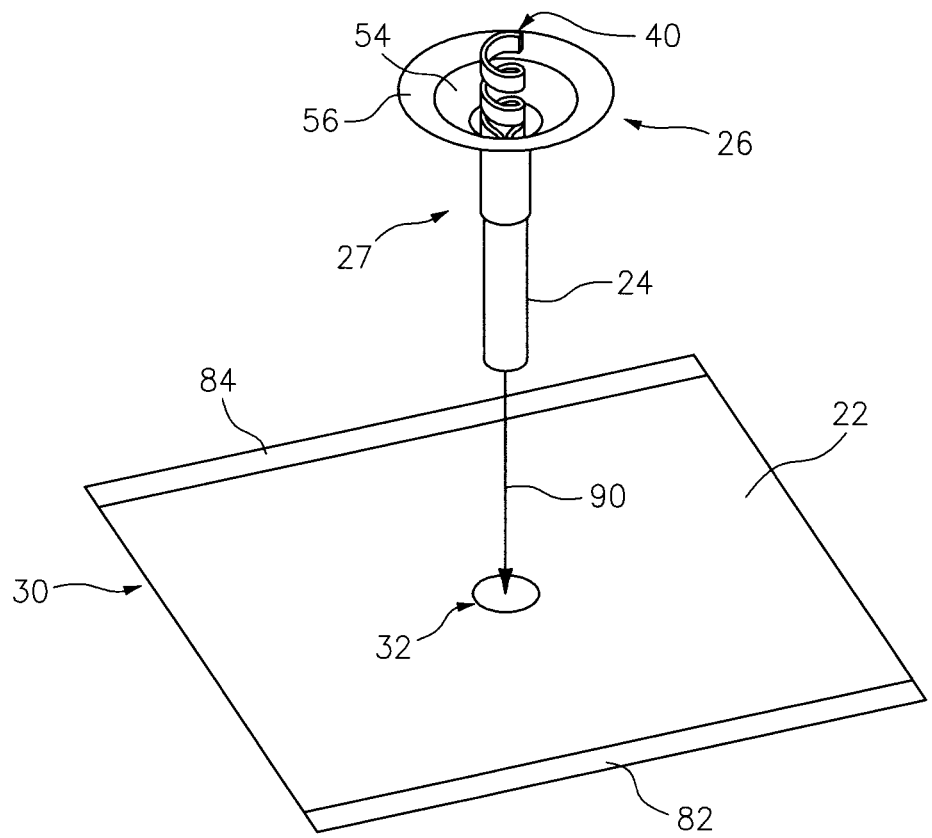
FIGS. 9 and 10 shows a tube assembly being inserted onto the dressing of FIG. 8 with the edge of the flange being sealed to the drape.
Figure 10:
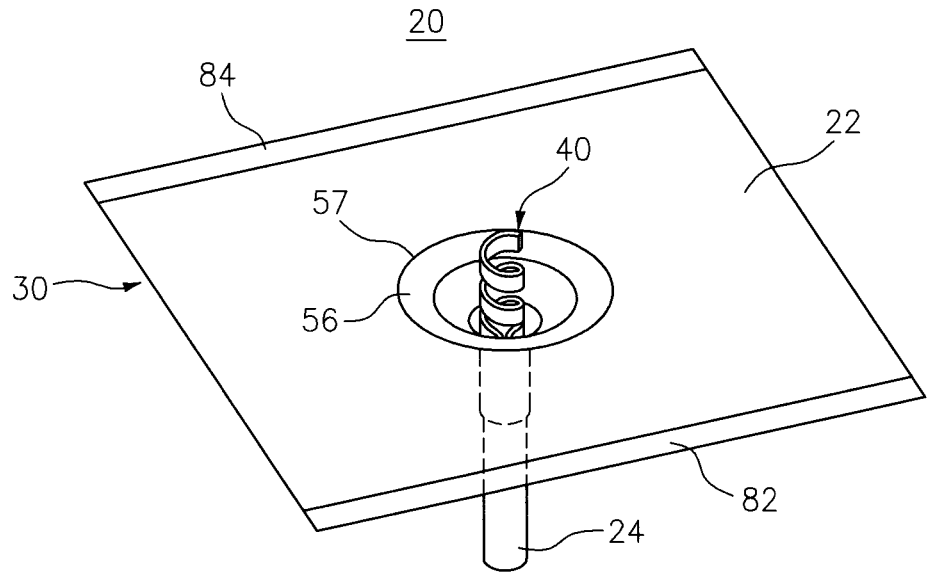

FIGS. 9 and 10 shows a tube assembly 27 being inserted, arrow 90, onto the dressing of FIG. 8 with the adhesive region 56 to edge 57 of the flange 26 being sealed to the drape 22 utilizing the pre-applied adhesive. Additional adhesive or sealant can be added around edge 57 or pre-applied to region 56 as desired.

Figure 11:
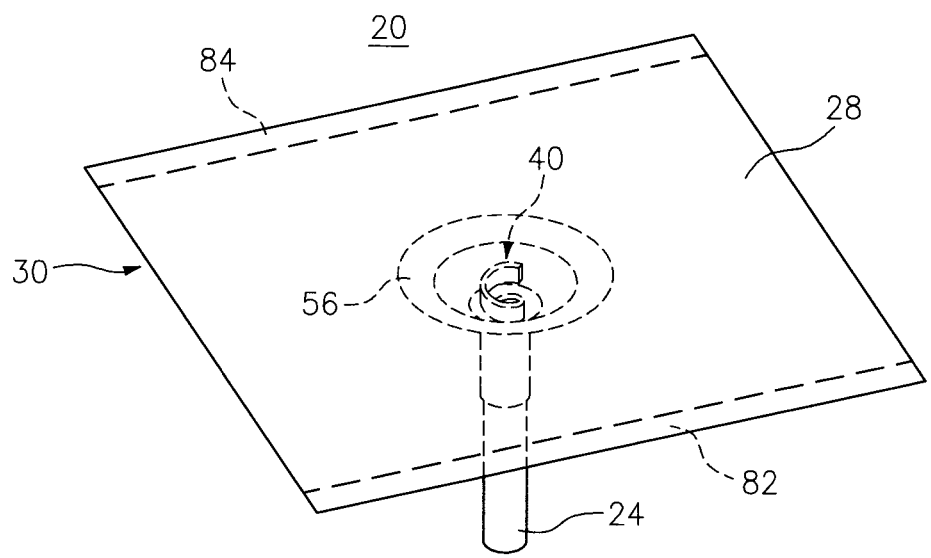
FIG. 11 shows a protective liner being added to the dressing of FIG. 10.
Figure 16:
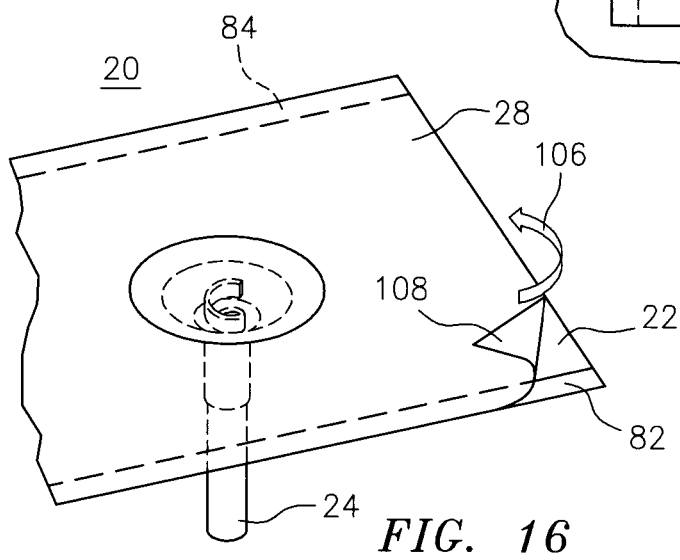
FIG. 16 is a perspective view of the underside of the dressing of FIG. 11 with the bottom, inner protective layer being removed.

FIG. 11 shows a protective liner 28 being added to the dressing 20 of FIG. 10. Protective liner 28 protects the skin-side adhesive, when pre-applied, until liner 28 is removed as illustrated in FIG. 16 below. Distal end 40 with anti-clogging feature 42 is sufficiently relaxed and short in length to be contained under liner 28. Liner 28 preferably extends beyond drape 22 over regions 82 and 84 of liner 30.

Figure 12:
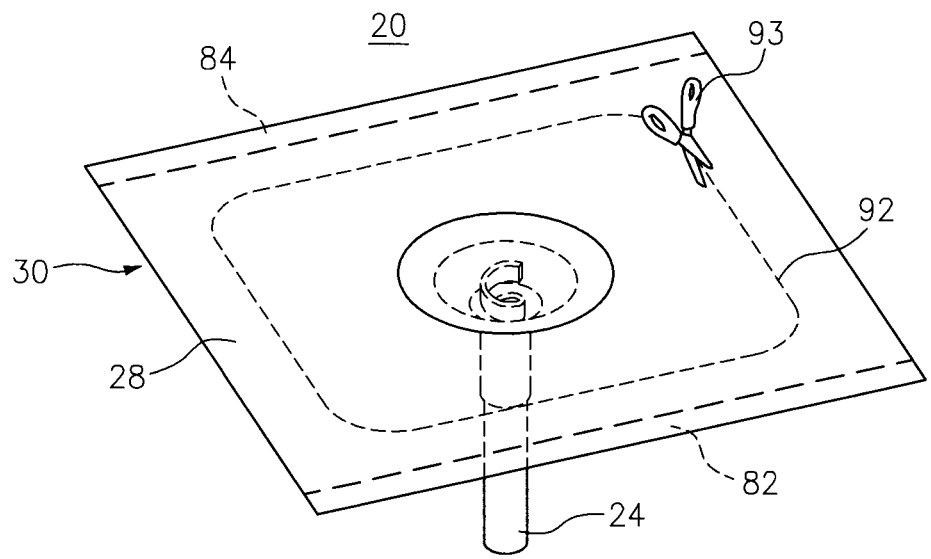
FIG. 12 illustrates how a user can cut the dressing of FIG. 11 to conform to a wound.

FIG. 12 illustrates how a user can cut the dressing 20 of FIG. 11, along dashed line 92 using scissors 93 for example, to conform to a wound.

Figure 13:
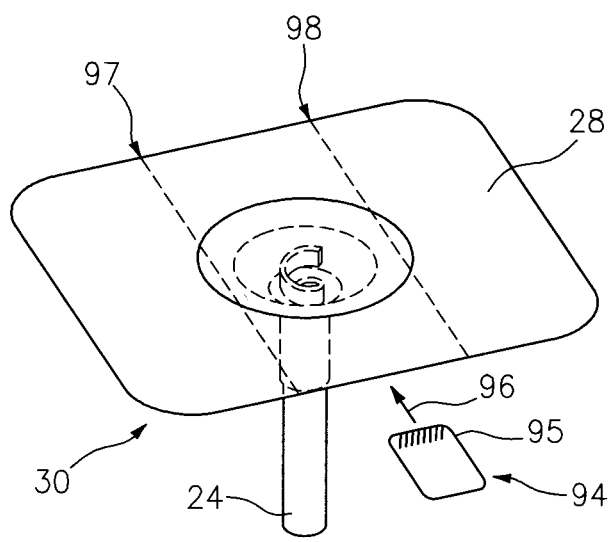
FIG. 13 shows a handling tab being added to the dressing of FIG. 12.
Figure 24:
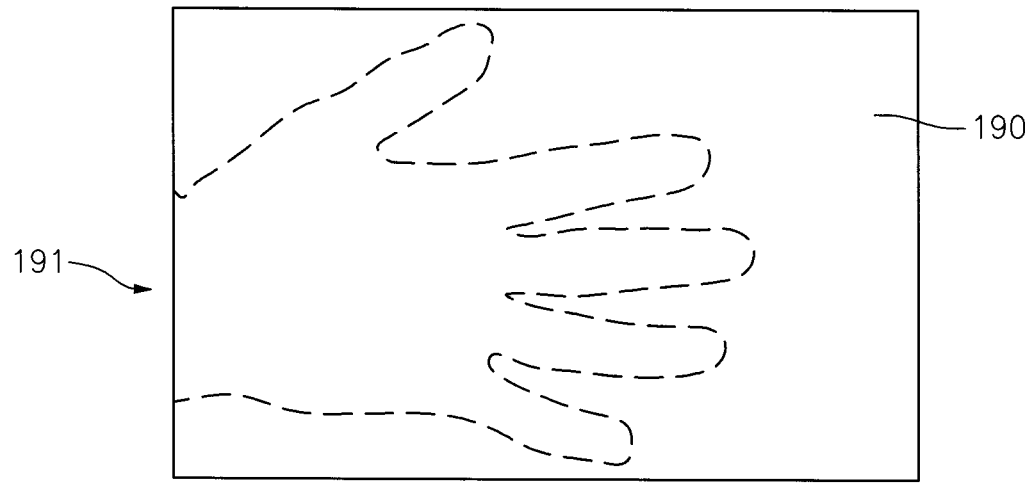
FIGS. 24 and 25 are schematic top plan views illustrating non-stick gloves and finger covers, respectively, integrated into a liner.
Figure 25:
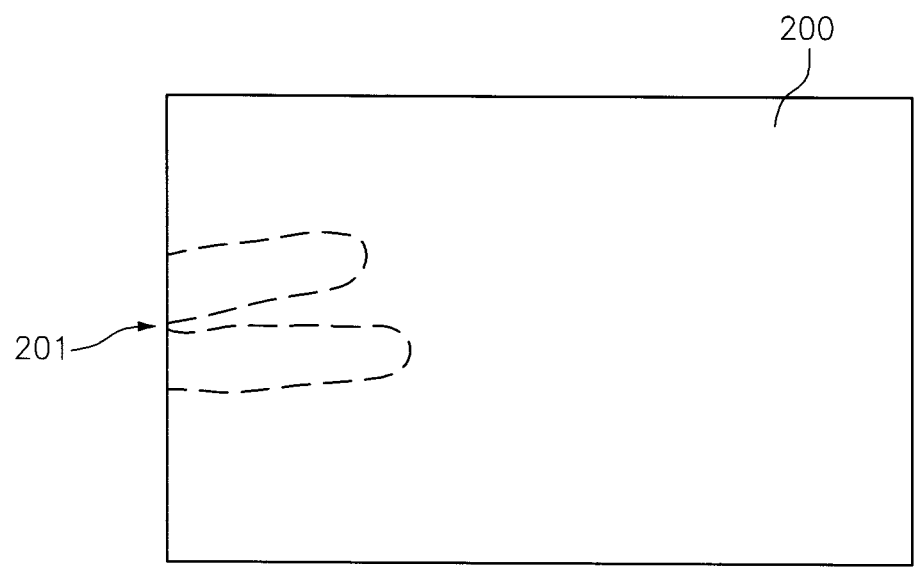

FIG. 13 shows a handling tab 94 being added, arrow 96, to the dressing 20 of FIG. 12, which is especially useful if liner extensions 82 and 84 are cut away. In this construction, tab 94 is attached by adhesive 95 to one of liners 28 and 30 to assist removal of the selected liner. Additionally or as an alternative, perforations 97, 98 create locations for easy removal of the liners. If perforations are utilized, it is preferred that the top and bottom liners have perforations that are aligned along different angles. The preferred angle difference is substantially perpendicular, that is, at about ninety degrees offset. Perforations are preferred when extensions 82, 84 are not provided. The dressings are very difficult to handle with medical gloves on, which are required for sterility. Therefore, handling tabs eliminate the need for the clinician to touch the adhesive. This is also desirable since powdered gloves tend to cause the adhesive to adhere to the powder and loose its adhesion properties. Another solution would be to provide non-stick finger or hand covers, such as shown in FIGS. 24 and 25, similar to the finger sealant applicator shown in FIG. 20. This is especially important when dressings are re-shaped, potentially cutting off handling features, and when the user is removing the top protective liner and folding down the top folds. Ideally, additional handling components are built into the packaging components or protective liners. Such as, the package that the drape comes in, turns inside out to form a sterile, handling glove, or the bottom liner is used to maneuver the higher-level of adhesive interactions when dealing with the top liner. The bottom liner may have a cut-out (pre-perforated) glove, FIG. 24, with the non-stick side, e.g. silicone-coated, initially facing the adhesive; preferably, a non-stick coating is provided on both sides for both right- or left-handed application.

Figure 14:
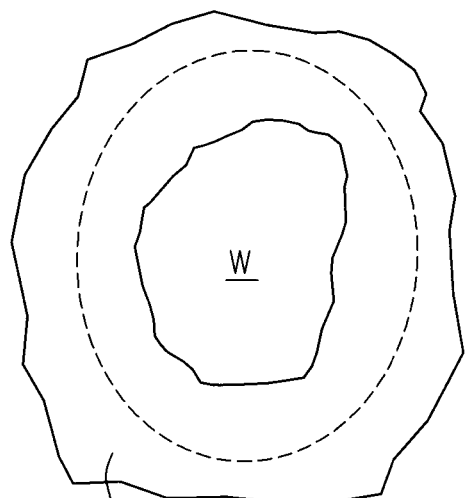
FIGS. 14 and 15 illustrate debriding and packing an open wound.
Figure 15:
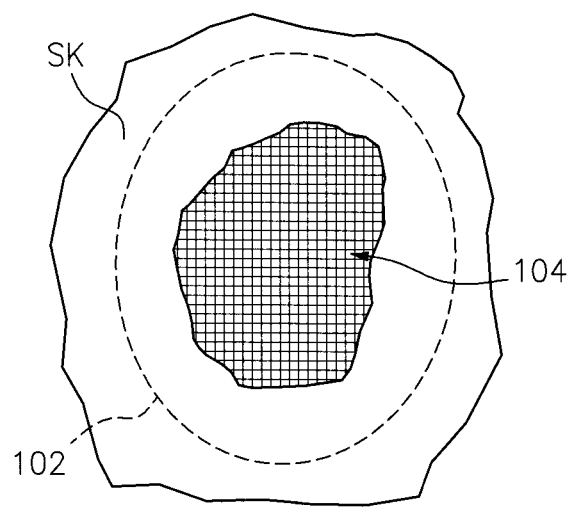

FIGS. 14 and 15 illustrate debriding an open wound W and cleaning the wound cavity and surrounding skin SK, preferably at least 3 cm in width as indicated by dashed line 102, with standard cleaning methods such as with alcohol and gauze wipes. Typically, the next step is to pack the open wound W with fluid pervious material 104 such as gauze, open-cell foam or a sponge.

FIG. 16 is a perspective view of the underside of the dressing 20 of FIG. 11 with the liner 28 being removed as indicated by arrow 106, such as by pulling on corner 108, to expose drape 22 with pre-applied adhesive.

Figure 17:
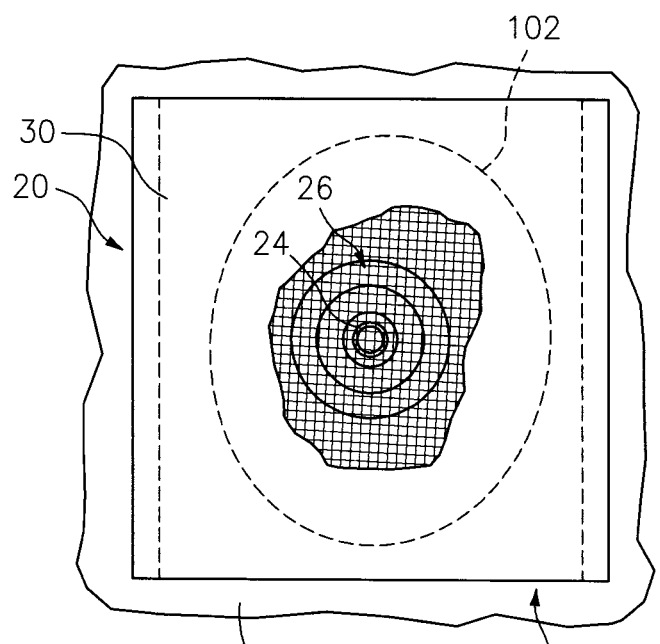
FIG. 17 is a schematic top plan view of a dressing according to the present invention attached to skin surrounding the wound.

FIG. 17 is a schematic top plan view of a dressing 20 according to the present invention attached via adhesive drape 22 to skin SK surrounding the wound. When negative pressure therapy is desired, a source of negative pressure is connected to tube 24 such that its lumen is in communication with the wound cavity.

Figure 18:
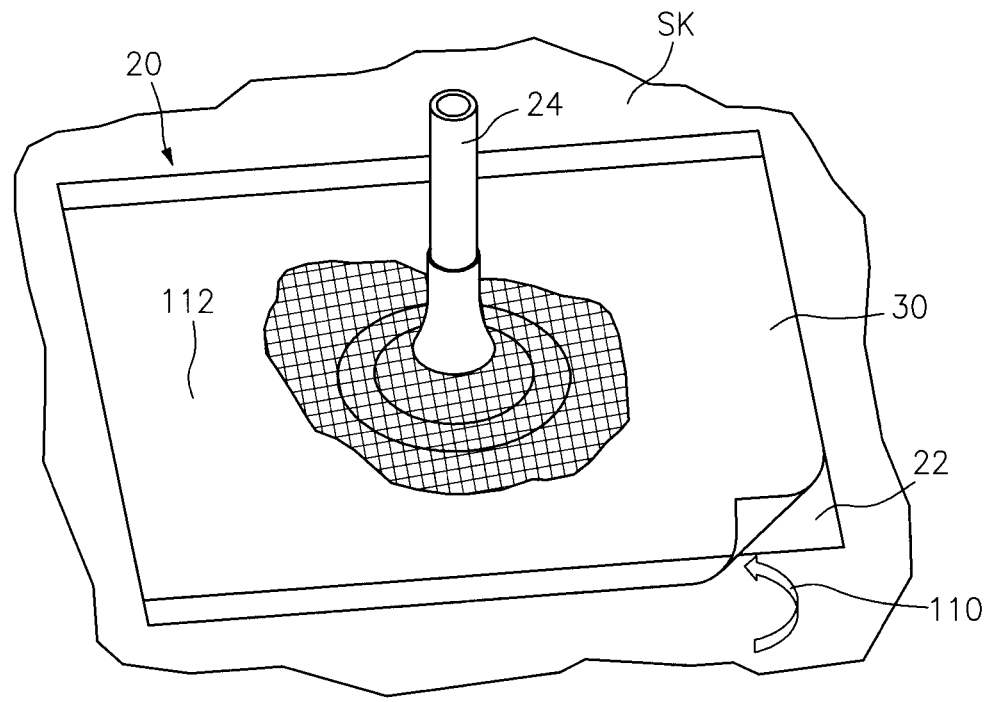
FIG. 18 is a schematic perspective view of the dressing of FIG. 17 with the upper protective liner being removed.

FIG. 18 is a schematic perspective view of the dressing 20 of FIG. 17 with the upper protective liner 30 being removed, as indicated by arrow 110. Dashed line 112 represents a perforation or pre-cut line to assist removal of liner 30 without sliding it over tube 24.

Figure 19:
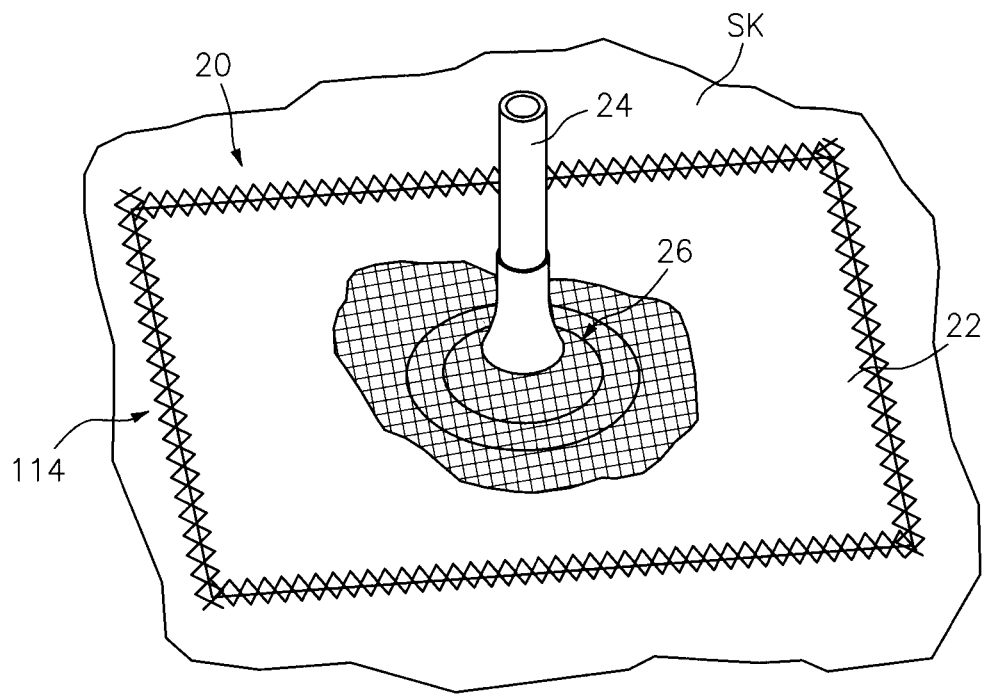
FIG. 19 shows liquid sealant being applied to the edges of the drape of FIG. 18.

FIG. 19 shows liquid sealant 114 being applied to the edges of the drape 22 of FIG. 18. The preferred sealant embodiment has as width of 2-3 cm and is centered over the edge of the drape 22.

If the dressing is applied to contoured surfaces on the body, such as described below in relation to FIGS. 29-30A, folds in the planar dressing may be necessary for adhering to the surface of the skin, in order to match the surface contour. These folds typically travel from the outer edge towards the tube 24. In this situation, the preferred application method is to minimize the number of folds by creating a few large folds. Preferably, there are no more than four folds, divided substantially equally around the periphery of tube 24. These folds are created when adhering the drape to the surface of the skin, forming a "T". Then, when the top protective liner is removed, the folds are adhered to the surface of the drape with the adhesive on the top of the drape. Preferably, the folds form individual triangles on the top surface of the drape. The folds are then pressed to lie flat and be completely adhered to the surface of the drape. Sealant is then applied to the edge of each fold to seal off the area between the fold and the top of the drape from the surrounding environment. This additional sealant preferably connects with the sealant placed around the outer edge 114, FIG. 19, for example. Preferably, the additional sealant is applied at substantially the same time as the original sealant with the same sealant material. Any drape material that would extend onto the skin, beyond the original edge of the drape, when folded preferably is cut off before pressing the folded drape material against the skin to lie within the original edge of the drape. Patterns may be provided on the upper protective liner to direct the user where to put the folds, when needed.

Figure 19A:
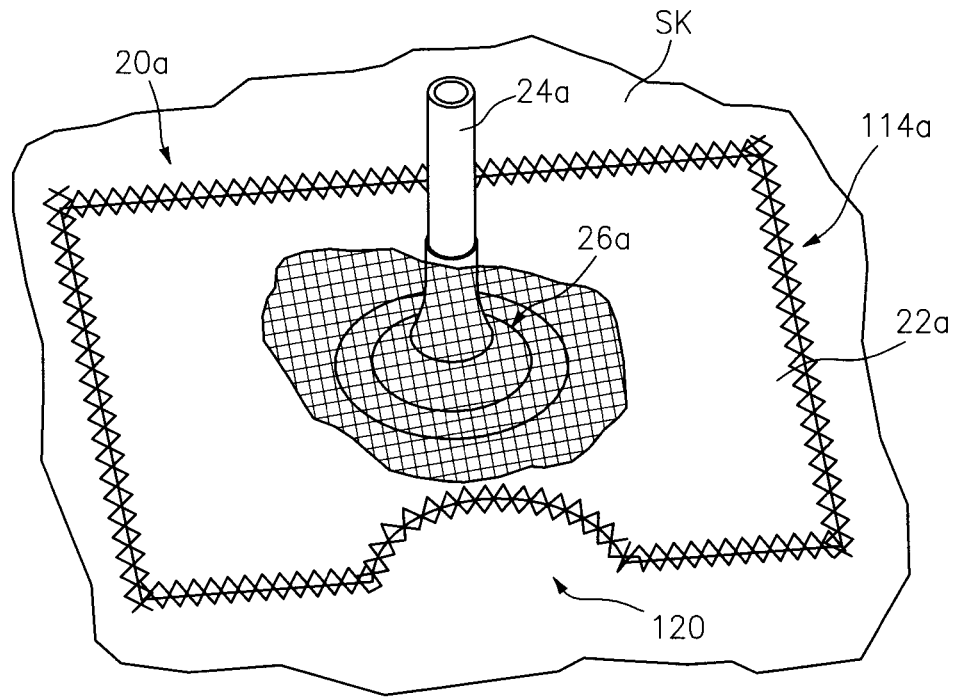
FIGS. 19A and 19B illustrate modifying the coverage of a dressing according to the present invention.
Figure 19B:
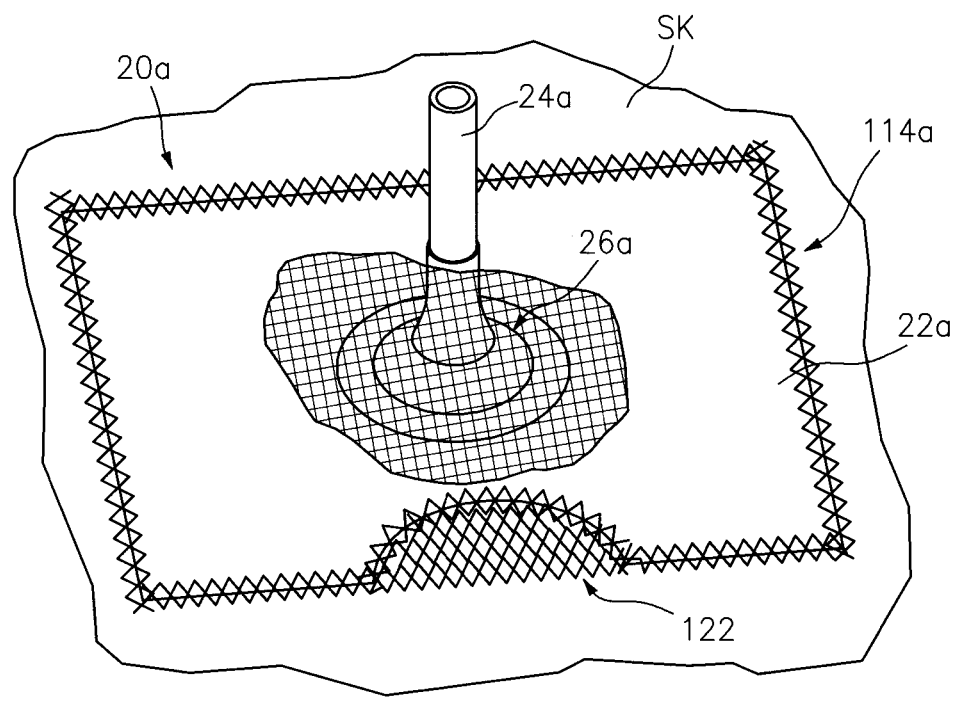

FIGS. 19A and 19B illustrate modifying the coverage of a dressing 20a according to the present invention, with drape 22a, tube 24a and flange 26a. If the dressing 20a is too small to cover the desired skin area around the wound, preferably by 3-5 cm, for instance if the user cut away too much of the dressing, as shown by cut-out 120, while reshaping the drape for easier application or in order to avoid a complex contour near the wound cavity, the user can use sealant to reconstruct the dressing as shown by additional sealant 122, FIG. 19B. A modified occlusive dressing 20a is thereby achieved. However, it is preferable for the drape 22a itself to cover the entire wound edge, in order to protect the wound cavity from the sealant material.

FIG. 20 is a schematic expanded view of a vial 130 of sealant, with closure threads 131 to receive a cap 134, with a non-stick finger protector 132, shown in cross-sectional view, preferably with a rim 133, optionally positionable within the vial 130 for storage and transportation.

FIGS. 21A and 21B show a dispensing apparatus 140 with removable cartridge 150 of liquid sealant. Dispensing apparatus 140 has a finger trigger 142 and a nozzle 144 in this construction and can be powered by a cylinder of compressed gas, such as a CO2 cartridge, contained within the housing 146. Preferably, the apparatus is gravity fed. Because there need not be a needle valve, such as found in typical air guns to stop the flow of fluid, an adhesive tab 152, FIG. 22, is initially removed from tip 154, and the cartridge 150 is inserted into the apparatus 140 as represented by arrow 149, FIG. 21B. A plug 156, FIG. 22, is then removed, such as by twisting, to expose an air hole at the top of cartridge 150 and activate apparatus 140 and allow sealant to flow or be sprayed out of nozzle 144. The apparatus 140 can be set aside temporarily, with nozzle 144 directed upwards, between sealant layer applications.

FIG. 22 is an enlarged perspective view of the cartridge of FIGS. 21A and 21B with internal chamber 160, raised floor 162, and slope 164 in this construction to assist gravity feed of sealant liquid to tip 154, as indicated by arrow 166. In other constructions, a multi-component sealant is delivered utilizing a separate chamber for each component. The components are mixed during delivery in a down-stream mixing chamber or in a mixing nozzle such as the 3M™ Scotch-Weld™ EPX™ Mixing Nozzle currently available from 3M Company, St. Paul, Minn. Other multi-component delivery systems can be utilized such as those commercialized by Henkel Loctite Corporation, Rocky Hill, Conn. One or more of the sealant components can be a powder or other state as long as the final sealant is delivered in a liquid state, including as liquid droplets via shearing or a propellant.

Figure 23:
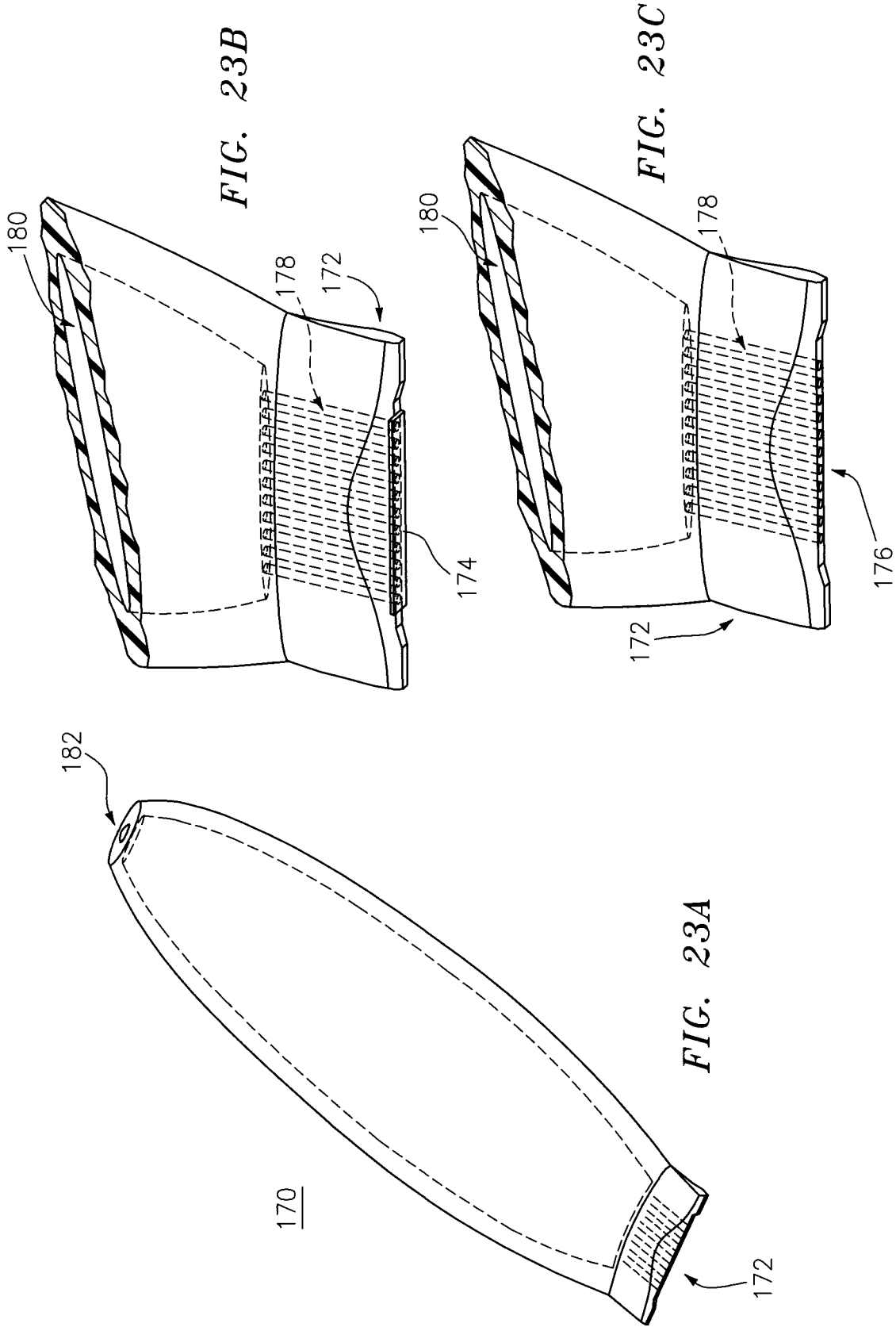
FIG. 23A is schematic perspective view of a hand-powered squeeze applicator for liquid sealant.
FIGS. 23B and 23C are enlarged views of the outlet with and without a removable strip covering the dispensing openings.

FIG. 23A is schematic perspective view of a hand-powered squeeze applicator 170 for liquid sealant.

FIGS. 23B and 23C are enlarged views of the squeegee-type outlet 172 with and without a removable strip 174 covering the dispensing openings 176 of passages 178 communicating with inner chamber 180. In this construction, a removable tab 182, FIG. 23A, allows air to enter chamber 180 during delivery of the sealant.

FIGS. 24 and 25 are schematic top plan views illustrating non-stick gloves 191 and finger covers 201 formed in liners 190 and 200, respectively. These applicators are non-stick, such as by a non-stick silicone coating, on only one side in some constructions and, in other constructions, are non-stick on two sides.

Figure 26:
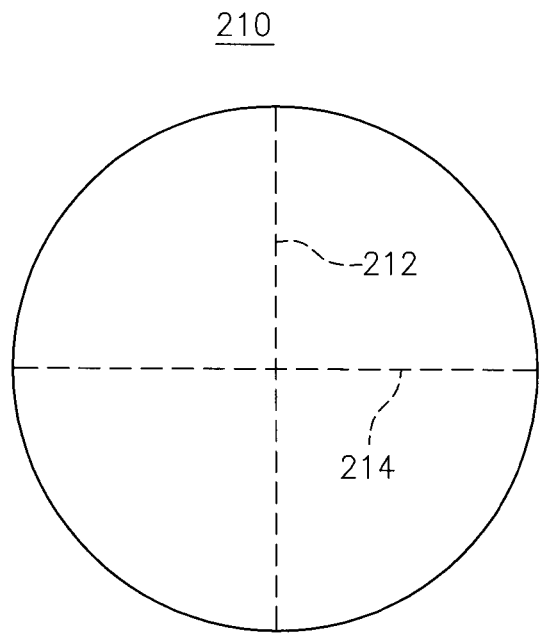
FIGS. 26-28 are schematic top plan views liners having different shapes.
Figure 27:
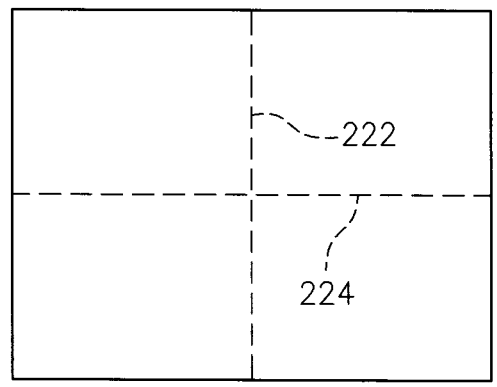
Figure 28:
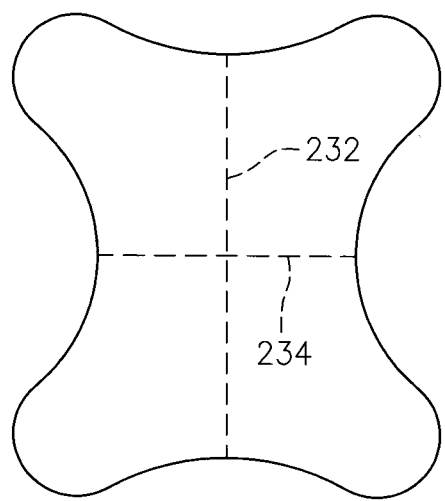

FIGS. 26-28 are schematic top plan views liners 210, 220 and 230 with indicator lines 212 and 214, 222 and 224, and 232 and 234, respectively, having different shapes for selected locations and contours of a patient. Shorter lines 222 and 234 have priority if folds are needed; a symmetrical shape such as a square or the circular shape of liner 210, FIG. 26, has fold lines of equal priority.

Figure 29:
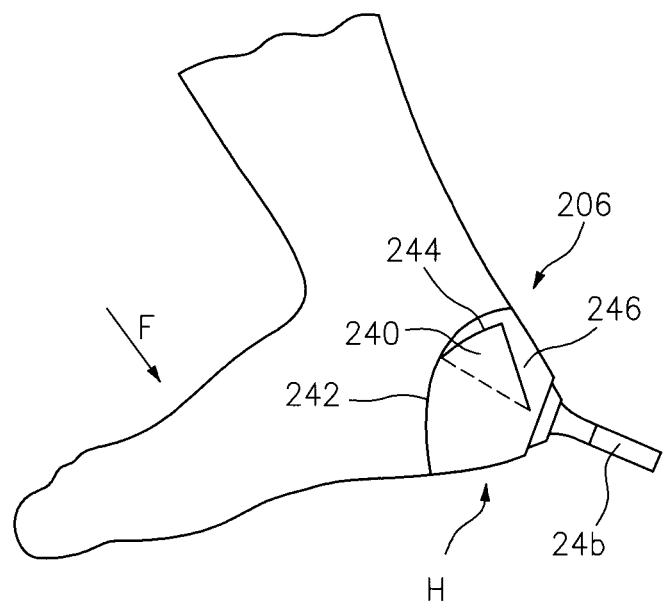
FIG. 29 is a schematic side view of a dressing according to the present invention being applied to the heel of a foot.

FIG. 29 is a schematic side view of a dressing 20*b* according to the present invention being applied to the heel H of a foot F. Flange 26*b* is positioned with tube 24*b* communicating with a wound in heel H. One large fold 240 is shown, with edges 244 and 246.

Figure 30:
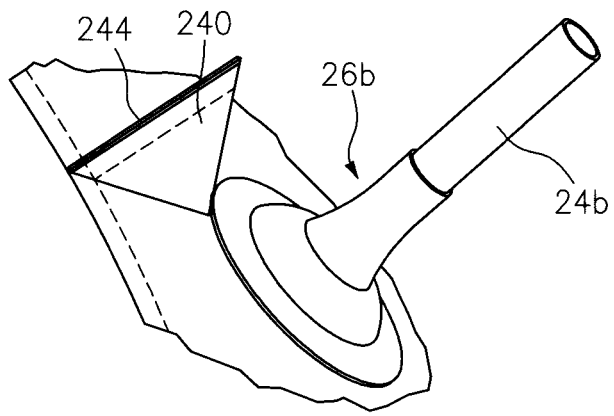
FIGS. 30 and 30A are enlarged schematic views of the dressing of FIG. 29 with a fold being created and then pressed flat to enhance conformance to the heel.
Figure 30A:
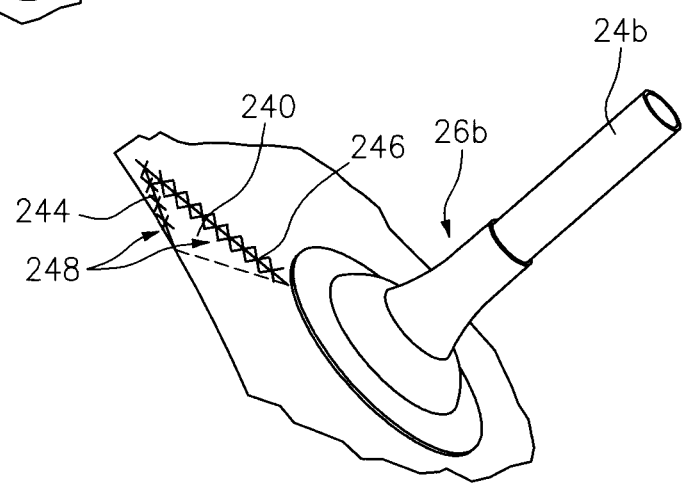

FIGS. 30 and 30A are enlarged schematic views of the dressing of FIG. 29 with a fold 240 being created and then pressed flat to enhance conformance to the heel. All edges 242, 244 and 246 should be sealed with sealant 248 according to the present invention.

There are multiple different methods of using the sealant described in this disclosure at the dressing-to-skin interface. The first method is to use the sealant in conjunction with current, commercial skin dressings (or dressings with similar embodiments), in order to achieve occlusive properties. In order to do this, the dressing is first applied to the skin, step 1502, FIG. 33, after the wound is packed, step 1501; typically, the dressing (a.k.a., drape component) is a planar adhesive tape form. The drainage tube may enter into the dressing at the dressing-to-skin interface, or it may have its own connector that requires an incision into the dressing above the wound cavity, step 1503. The dressing system is applied with its recommended procedure. Then, all dressing-to-skin interfaces are sealed with the sealant and potentially additional adhesive, step 1504.

At the dressing-to-skin interface, the sealant contact with the skin should be biocompatible. The sealant should conform to and seal off the folds and creases in the skin, which are often bridged when applying a standard, planar wound dressing. These cracks are a significant source of air leaks into the system without a liquid sealant with the proper wetting properties. The proper wetting properties are achieved by applying the liquid sealant directly to the skin and dressing in its liquid form through a painting process or through spraying the liquid with an atomization process that eliminates liquid run-off and that may achieve a more uniform, thin film.

Once a crack in the planar dressing exists, crack propagation may occur in tension and compression with reduced, applied strains. Therefore, sealing any initial cracks in the dressing-to-skin interface is desirable. Also, properly sealing the dressing-to-skin interface at the edge of the dressing deters any air leaks from future crack propagations, as the sealant hinders the propagation from reaching the outside environment. If an additional adhesive is used between the sealant and dressing-to-skin interface, then the adhesive should adhere to the skin, dressing, and sealant to form the necessary bond strength. The adhesive or its applied components should also conform to the folds and creases in the skin and/or dressing. The adhesive should be compatible with the skin, dressing, and sealant when applying the adhesive under the sealant, or when mixing the sealant with an adhesive component prior to application.

Use of the liquid sealant can permit elimination of the current commercial dressings (or similar dressing embodiments; a.k.a., the drape component). The liquid sealant can be applied directly over the wound cavity and wound packing material. In some embodiments, the packing material may require an additional liquid tight barrier if the liquid sealant can be absorbed into the packing material. Additionally, a liquid tight barrier may need to exist at the interface between the packing material and the wound edge, as the sealant could potentially leak into this barrier, depending on the application technique of the packing material, which may not be desirable. A gap at the interface between the packing material and the wound edge may be disruptive to the sealant in creating a continuously occlusive film, or the potential of the sealant contacting the inside tissue of the wound cavity may need to be eliminated. These barriers may be of an occlusive nature; in this case, the sealant should be applied at any of their non-occlusive edges; however, the sealant may also cover the entire surface area, which may help to maintain the adhesion of the barriers. The barriers can be made of multiple materials from adhesive and non-adhesive polymer films to clays and pastes, for example. Barriers mentioned in this description are different from the standard wound dressings, as the standard wound dressings' adhesion to the skin forms structural and adhesion integrities of the dressing-to-skin interface, and the barriers currently discussed are used to protect the wound from the sealant component and are not necessarily intended to provide any structural support beyond that purpose.

Maceration of the skin under a truly occlusive dressing may be of concern to the caregiver. This can be solved with a material selection solution, as a one-way, directional occlusive sealant material can be used that allows the skin to breathe and its moisture to evaporate without letting air into the system. Similar material properties are commonly found today in materials used for sports apparel. Additionally, this can be solved from a design perspective. The sealant application area can be made narrow enough that the moisture of the tissue under the dressing can diffuse around the seal. If a larger surface area of seal adhesion is necessary, a web of sealant can be applied to allow diffusion around the webbing. Additionally, the sealant can vary in thickness via the atomization process, where a thick enough dressing for occlusive properties is sprayed around the wound edge or dressing-to-skin interface. This application can maintain a narrow width, and then the rest of the dressing can be made into a thinner layer that is breathable based on a different number of lamination layers or by using different spraying variables and techniques. This thinner part of the dressing can maintain a continuous film embodiment with the occlusive barrier, as the debonding energy of the thinner part is significantly decreased due to the reduction in thickness, increasing the effective bond strength. Additionally, this breathable component can be webbed over the surface, instead of encompassing a continuous film embodiment.

The tube-to-dressing interface should be sealed if the connection is not prefabricated to be occlusive during its manufacturing process, as it is in the Spiracur dressing. The sealant should bond to both materials found at the tube-to-dressing interface and form an occlusive seal spanning the interface, step 1504, FIG. 33. Three methods can be used for this sealant interface and its components: 1) dressing components that were not originally prefabricated to be occlusive can be pre-assembled and sealed prior to dressing application (most desirable from an occlusive results reliability perspective); 2) dressing components can be preassembled prior to dressing application, but the seal is applied after dressing application; or 3) the tube connection method is fabricated and sealed to the dressing during or post dressing application.

The first method provides the user with a method to prefabricate a custom dressing that has an occlusive tube-to-dressing interface. This eliminates many potential air leaks, and for the first time, allows custom, prefabricated, occlusive dressings to be made in the clinical setting. Method two is convenient if the liquid sealant is the same for all dressing interfaces; therefore, all the interfaces (tube-to-dressing and dressing-to-skin) can be sealed in one step after the dressing application. However, this method requires that the pre-assembly configuration is stable during its application, before any sealant is applied. For method three, less prep-work needs to be performed by the caregiver. If this sealant method is ergonomic and repeatable without any prefabrication, then this method can significantly cut-down on dressing time, which is a significant personnel and cost savings for the care center. The ergonomic and repeatable characteristics depend on the tubing connector designs.

Multiple tubing connector designs can be manufactured for sealing purposes to be used for all three methods. Three basic design concepts can span many embodiments. These three design concepts are:

1) Puncture the dressing with the drainage tube, such that the drape fits snuggly against the tube. Then, apply the sealant at the tube-to-dressing interface. With this method, the tube can recess into the wound cavity at a custom length as indicated by extended distal end 1801, FIG. 36. If the adhesion force of the sealant needs to be increased, an additional adhesive can be added under the sealant or mixed with the sealant, or the tubing and/or dressing can be pre-coated with a material that the sealant has an affinity for. In practice, rubberized polymers typically have a strong affinity towards themselves, even if the under layer is previously cured. Multiple drainage holes, as illustrated in FIG. 4, or a spiraled cut pattern, FIGS. 2 and 3, in the portion of the tube extending into the dressing is preferred, in order to prevent the tube from occluding against saturated packing material or with particles in the wound exudate.

2) The same concept as in concept 1, except with a different tube entry into the dressing. This concept is for the case where an initial planar dressing is used. Two pieces of the planar dressing cover the wound from two different sides, and they meet above the wound cavity in a "T" joint. The tube is placed through this "T" joint into the wound cavity before the "T" joint is sealed. Then, all of the interfaces are sealed with the liquid sealant.

Figure 36:
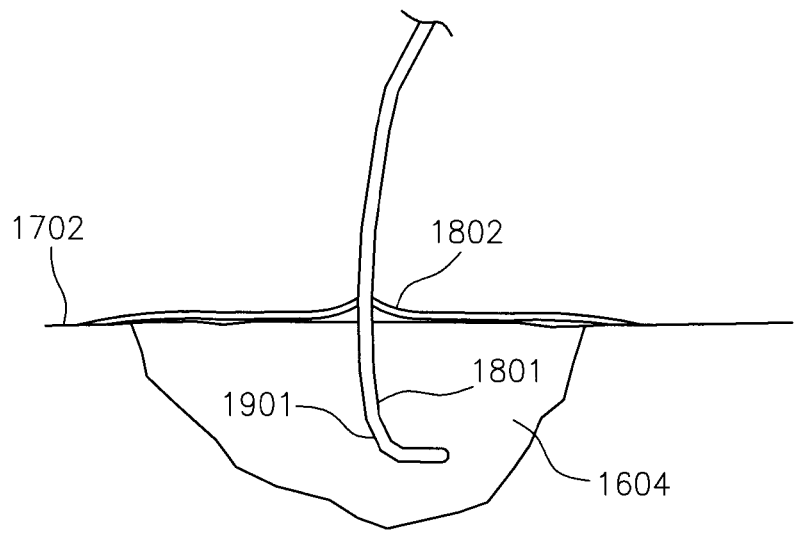
FIG. 36 is a diagram of some of the specific components of an occlusive wound dressing embodiment.

3) The same concept as in concept 1, except at the tube-to-dressing interface, a prefabricated foot 1802, FIG. 36, also referred to herein as a flange, is attached (preferably air-tight) to the tube in order to provide a planar surface to seal to the dressing. In one functional embodiment, the foot 1802 is made of a flexible material that the sealant has a strong affinity for and no additional adhesive is necessary. The material of the foot may be tapered in thickness, such that it thins to meet at its edge(s) with the dressing, which may be more desirable for reliable, occlusive sealant application. The tube can connect to this foot 1802 in many orientations; however, it is often preferable to minimize the dressing profile. However, often when minimizing the dressing profile, the tube is in an orientation that cannot be readjusted after dressing application. Therefore, the tube may connect perpendicular to the skin surface, and by using non-kink tubing and/or the flexibility of the foot 1802 material allows the tube to be oriented in any orientation post dressing application, such that the tube will not kink and occlude itself. For this concept, the tube may not puncture the drape, but instead, the hole (a.k.a., incision) may be pre-cut; the foot should extend beyond the hole (a.k.a., incision).

Figure 37:
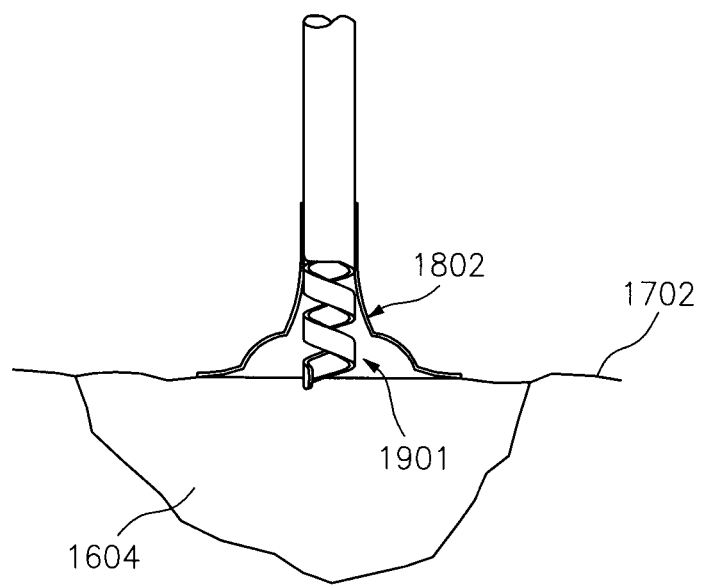
FIG. 37 is a diagram of a tube connection method with a spiral end tube.

4) The fourth concept is the similar to concept 3, except the tubing does not extend into the wound cavity, FIG. 37. Therefore, an incision is made into the dressing, and the tube opening is positioned over the center of the incision, as in the T.R.A.C. Pad. The foot should extend beyond the incision and is sealed to the dressing with the liquid sealant or occlusively pre-sealed during its manufacture. In this embodiment, the end of the tube should be designed to stop potential occlusion onto the foot, onto packing materials, or with wound exudate substances. Therefore, if the foot is connected to the tube above the skin surface, the end of the tube may have a spiral cut along its length, up to its interface (intersection of the upper portion of foot 1802 and tube distal end 1901 in FIG. 37) with the foot. Additionally, an anti-occluding material may be placed at the end of the tube between the foot and the dressing. This anti-occlusive material may be a large pore, open cell sponge.

In the tube-to-dressing connection, as with all sealed interfaces, an additional adhesive may be added if the bonding strength needs to be increased. The foot may also be initially adhered with a tape or adhesive to the dressing prior to sealant application. The tube connectors can exist in many similar embodiments to those listed above; however, a limited number of examples are given here in order to illustrate the basic connections and the occlusive dressings. The tube-to-dressing interface may be occlusively pre-sealed during its manufacture. Additionally, the component attached at the interface may only consist of a tube connector (which may or may not contain a segment of tubing) that is additionally connected to a longer piece of tubing that then attaches to the pump. Examples of occlusive tube connectors are barbed connectors that connect directly with a tube, specific connectors that interlock with each other and are required on each end of the connected components, and a compression fit seal such as a cylindrical hole in rubber that the tube can be occlusively pressed into.

As previously stated, handling a dressing with a planar tape embodiment may cause the adhesive to weaken prior to dressing application. Therefore, specific handling devices for the caregiver can be included with this dressing component. These devices may include non-stick gloves, such as PTFE gloves, FIG. 24, or non-stick fingertips, FIGS. 20 and 25. Handing tabs that extend from the dressing may also be incorporated into the dressing design. These tabs may be a part of the dressing (a.k.a., drape) that are torn-off after applying the dressing, or they may be extensions of a removable backing material that is attached to the dressing as shown in FIG. 13.

For application of the sealant, many application embodiments and methods are possible. For mechanical applications, including painted applications, the applicator embodiment can be a brush, roller, sponge, spatula, or other similar embodiment to apply paint in a "spreading" fashion. These spreading devices can be attached to a container (preferably refillable) of liquid sealant for a continuous feed of sealant to the applicator; this may be gravity fed (passive or user controlled), or the applicator may be prepped with sealant by dipping the applicator into a container of sealant. Although painting is not the preferred application method for the liquid dressing, it may be preferred if a high viscous sealant material is used to span large gaps, such as that between the packing material and the wound edge, the potentially high ridges of a hydrocolloid at its skin interface, or the large creases, gaps, and folds in a hydrocolloid dressing, due to its high stiffness and thickness and geometrical mismatch.

For sprayed applications, the device to atomize the sealant with a shearing process can be a refillable spray gun or airbrush, with an external pressurized gas supply, or this functionality can be incorporated into a miniature, handheld spray can, which can be rechargeable and refillable. Each embodiment has a design specific envelope of pressure, velocity and volume flow of gas that is required to shear the sealant, such that it forms a thin film, continuous layer on the skin. If the operation is outside the envelope, the droplets of the spray may be too large and will not spray as a continuous layer, but will sputter onto the skin, or the gas may not shear the fluid out of the fluid opening. In a functional embodiment, the liquid sealant is gravity fed into a center opening in a nozzle, and pressurized gas shears the sealant through a circumferential ring around the sealant nozzle opening. Multiple nozzles may exist for one or both fluids. Particularly, the spray pattern may be controlled through the shearing of the sealant from multiple gas ports, aimed in different shearing directions across the liquid sealant nozzle. In a handheld device, the pressurized gas may be generated from a miniature gas cylinder, such as a high pressure, liquid carbon dioxide cartridge. The spraying device may be charged by the caregiver when he or she activates the charged canister of gas.

Figure 33:
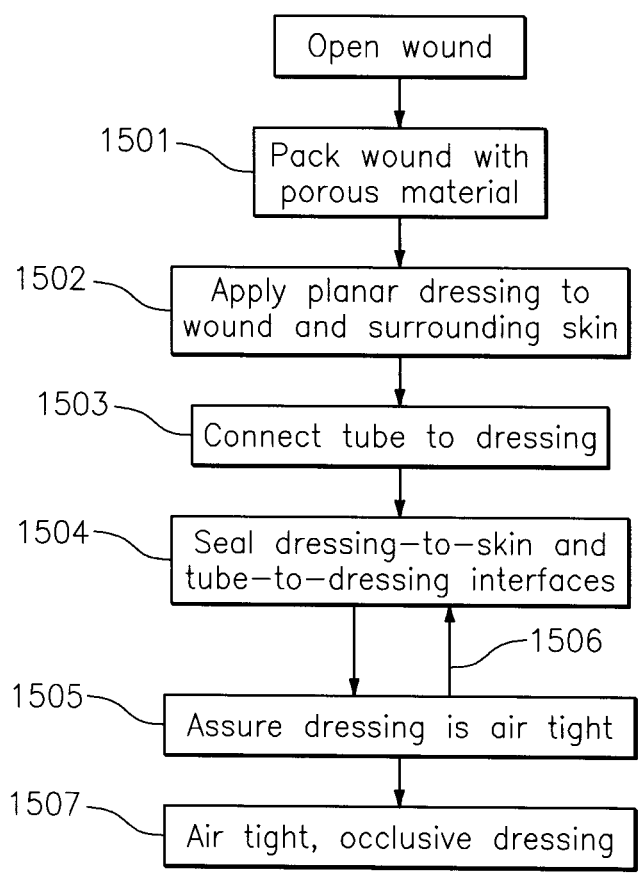
FIG. 33 is a flow chart of a sample occlusive dressing method.

Once the dressing-to-skin and tube-to-dressing interfaces are sealed (either during dressing application or during its manufacture), the caregiver should monitor the pump to assure that air is not leaking into the system above a predetermined threshold, typically zero, step 1505, FIG. 33. This can be done visually, for example, by monitoring the expansion of the pump (a.k.a., mechanical pump) or with an air leak test that is further disclosed in the pump descriptions, or it can be sensed using pressure sensors to detect the vacuum pressure over time (particularly, with a mechanical pump, if the pressure changes continuously with internal pump volume). If too high of an air leak exists, the dressing-to-skin and/or tube-to-dressing interfaces can be resealed with the liquid sealant by removing the previously applied sealant material, or overlaying the new sealant over the previously applied seal material, step 1506, FIG. 33. This is an iterative process until the desired air leak threshold is achieved, step 1507.

Figure 34A:
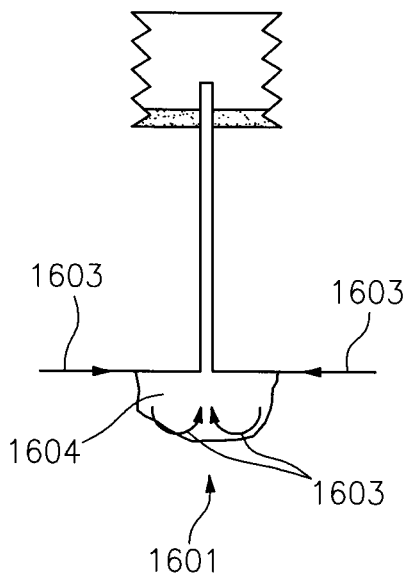
FIGS. 34A and B are diagrams comparing active versus passive flow NPWT systems.
Figure 34B:
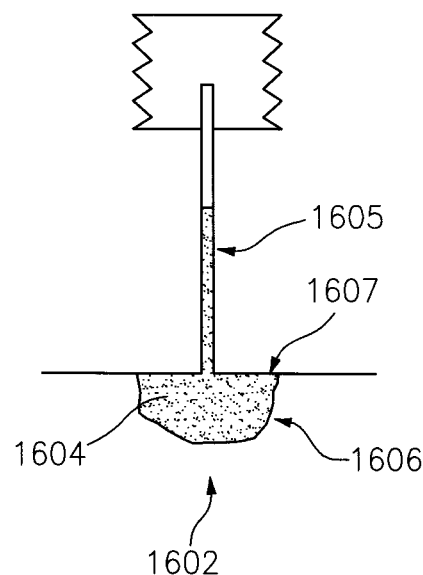

When a truly occlusive wound dressing is used for NPWT, the behavior of the system changes from an active flow system, FIG. 34A, to a passive flow system 1602, FIG. 34B. When air leaks, arrows 1603, FIG. 34A into the active system, the system has an active flow of fluid (both air and wound exudate) that both removes the exudate from the wound cavity 1604 and tends to dry out the wound cavity. With an air-tight system 1602, FIG. 34B, the flow of the exudate toward the pump is no longer an active flow, but tends to build up, 1605, even into the tube over time, maintaining a passive flow to the vacuum source. A pressure differential still exists at the surface of the wound bed 1606 and, thus, negative pressure is still being applied to the wound bed; however, the wound cavity volume 1604 fills with exudate fluid 1605 over time. This characteristic may have increased healing benefits compared to standard NPWT, as it maintains a moist, healing environment at the wound site, while also maintaining NPWT vacuum pressure benefits.

Figure 35:
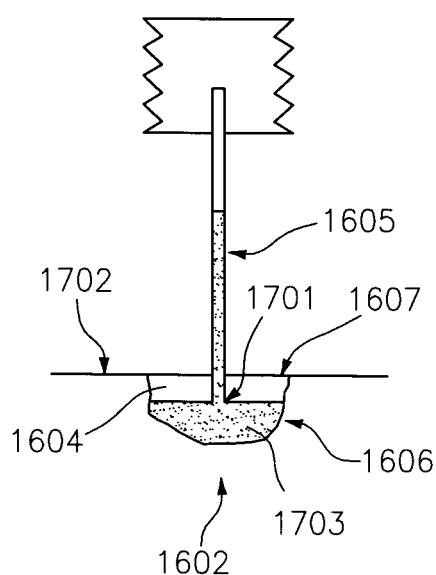
FIG. 35 is a diagram of a method to prevent undermining of the dressing due to exudate build-up in the passive NPWT system.

With this build-up of fluid 1605, FIGS. 34B and 35, the dressing-to-skin interface adhesion 1607 may be compromised over time by the exudate, and the exudate may eventually undermine the dressing and leak out of the dressing-to-skin interface. The rate of exudate removal, size of the wound cavity, and time between dressing changes determine the build-up characteristics. If there is a chance that the dressing may be compromised, it can be prevented with multiple methods, including:

1) A sealant or additional adhesive that can withstand the exudate build-up may be applied. For this case, the sealant and/or additional adhesive should be applied as close to the wound edge as possible. This is difficult if a standard dressing was used. Planar dressings typically leak over the three-day dressing period if fluid build-up occurs. This is because the exudate often degrades the adhesive by undermining the dressing at the wound edge at the locations of initial creases in the dressing. Therefore, a dressing without initial cracks at the wound edge is preferred; however, the dressing application described in the previous section only seals the outer edge of the dressing. To solve this problem, a flexible adhesive, with flexibility and adhesive properties such as those of a 30+ day silicon wig glue, may be initially applied at the wound edge under the adhesive planar dressing. This can fill in any initial cracks at the wound edge and prevent exudate-caused degradation.

2) A barrier can be applied at the wound edge, after the wound packing material is inserted. This barrier may be made of highly absorbent material, in order to reduce the chance of overspill of exudate due to factors, such as gravitational effects.

3) The tube end can be recessed into the wound cavity below the plane of the surface of the skin 1702, as indicated by arrow 1701, FIG. 35. Therefore, the drainage line of fluid 1703, and hence the build-up of exudate will not build-up to the wound edge 1607, and degrade the adhesive. This technique may not be possible if the wound is superficial.

4) A purge valve to let a controlled, temporary air leak into the dressing system to clear the fluid can be incorporated into the dressing system. This valve can be incorporated using the same connection methods as described in the Tube-to-Dressing Interface section in this disclosure. This would cause the fluid to actively flow into the fluid collection canister during the initial pressure drop in the system. The pump can be reset, if necessary.

5) The wound packing material can be made from materials with a low resistance to the flow of exudate and a low absorption, which would encourage the fluid to passively move through the system at a faster rate in a path more direct to the drainage tube. Depending on the rate of exudate removal, this may not fix the problem if it is a very low rate. In this case, the packing material should be designed to direct flow to the drainage tube and specifically away from the wound edge.

6) If the dressing is fabricated completely out of the liquid sealant (potentially with an additional adhesive) with no planar dressing component, then no cracks will exist at the wound edge when it is properly applied, and therefore, no cracks will initially exist for the exudate to undermine.

Although any mechanical or electrical vacuum source may be applied to the occlusive dressings in this disclosure, a mechanical system may be preferred due to the significant benefits over electrical pumps. Mechanical vacuum pumps and methods are provided for medical application in negative pressure wound therapy (NPWT) that would be compatible with the disclosed dressings. A number of known pumps are described by the present inventor in "Development of a simplified Negative Pressure Wound Device" submitted in 2007 for her Master of Science in Mechanical Engineering at the Massachusetts Institute of Technology. The pump is initially set and then governed by a linear or non-linear spring force. The pump enclosure may act as a collection chamber; however, a separate collection chamber may exist in series with the pump.

Figure 31:
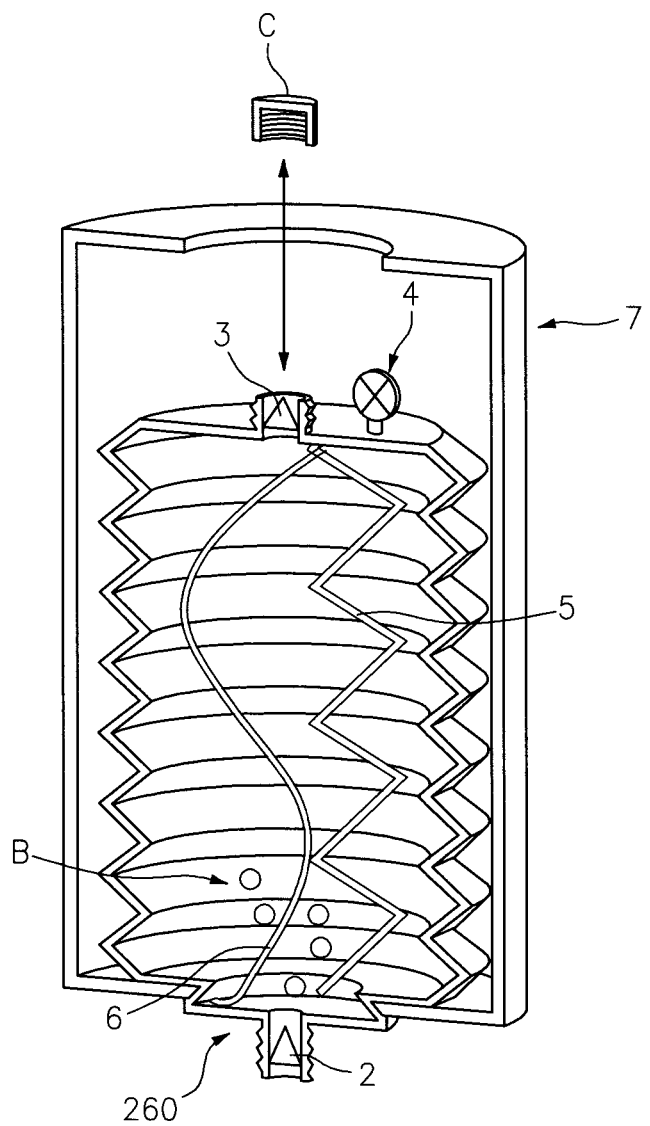
FIG. 31 is a cross-sectional view of a known bellows pump.

In one embodiment, the pump is a plastic bellows, shown in FIG. 31, where the enclosure and spring can be the same component. The pump is compressed manually and then attached to the tube of the wound dressing. A negative pressure is applied through expansion of the bellows due to the spring characteristics of its material and design. The pressure gradient of the device continuously decreases over the expansion of the standard bellows due to its linear spring-like properties. Referring to the above description, one skilled in the art would realize that other embodiments exist: the device could be constructed of a different material bellows, and/or the device could contain an additional spring 5 in parallel with the bellows in order to vary the spring constant without changing the material properties and design of the bellows itself. If there are no air leaks into the system, then the bellows would remain at a constant expansion length, and therefore, at a constant pressure. The bellows can be collapsed to any desired therapy pressure from maximum compression to zero.

Figure 32:
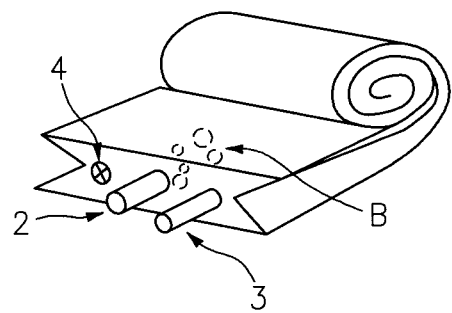
FIG. 32 is a perspective view of a novel rolling bellows pump.

In addition to the standard bellows, another embodiment of bellows can resemble a constant force spring, in order to decrease the pressure gradient. In one embodiment of this design, the bellows resembles a long tube that, when fully compressed, is rolled onto itself, similar to a tape measure, as shown in FIG. 32. As it unrolls and expands from its flattened to open cross-section, it creates negative pressure in the tube to which it is connected. For the tube to unroll following the expansion of the bellows, the spring constant of the bellows must be higher than the spring constant of the constant force spring unrolling. The unrolling can also be mechanically dampened, for example by adhesion, or forced to unroll after expansion by structural limiters. In this embodiment, a long, cylindrical tube can replace the bellows, as it presents similar characteristics.

In all of the pumps described above, orientation of the device is independent of the magnitude of negative pressure pulled and the proper operation of the device. Therefore, the device is highly transportable. Referring to the above descriptions, one skilled in the art would realize that other embodiments exist; however, only selected embodiments are described in detail. To change pressures in a pump design, separate pumps can be made with different material properties and/or dimensions, or components can be swapped for different pressure results.

The negative pressure generated is governed by the material and mechanical properties of the container and/or balloon and the spring constant. Using a non-constant force spring (such as a common linear spring 5, FIG. 31, the pump may be used for negative pressure wound therapy that does not require a specific, constant pressure (in the case that the internal volume of the pump is expected to expand), although the variance in pressure can be reduced through material property selection and design. Using a constant force spring with a constant area, a constant vacuum pressure can be pulled throughout treatment, even if there is a change in the internal volume of the pump. This is the basis for design of the rolling bellows (FIG. 32), and the syringe concept discussed in the next section. Additionally, a more constant pressure with pump expansion can be achieved with a non-constant force spring by designing the force/area ratio to be constant, such as the balloon design with a small (constant) diameter to length ratio and a bellows with a varying cross-sectional area. Additionally, constant pressure can be achieved over time if no air leaks into the system, causing geometrical changes in the pump configuration. In this case, the pumps should be made out of materials that do not degrade when applying negative pressure overtime due to properties such as stress relaxation.

The pump is initially set and then governed by gravity. It includes an expansion container that expands due to an applied force such as a weight. The pump enclosure may act as a collection chamber; however, a separate collection chamber may exist in series with the pump. In one embodiment, the pump includes a rolling diaphragm syringe (similar to a friction free diaphragm air cylinder). Negative pressure amplitude is governed by the diameter of the syringe and the magnitude of the attached weight. One skilled in the trade would realize that a similar device could also be constructed of any sealed piston syringe. Referring to the above descriptions, the device could also include a linear spring in parallel with the syringe or a constant force spring in series with the syringe for expansion, eliminating the need for weight. This embodiment would then fall under the spring governed pumps described in the previous section. A rolling diaphragm can also be achieved using a rubber ball design. One hemisphere of the rubber ball is held rigid in its inflated position, such as by bonding it to the inside of a rigid hemisphere, and the other hemisphere is compressed into it. The embodiment of the pump resembles a bowl. Then, the bowl is oriented so that its hollow side is facing down. A weight is hung from the ball (i.e., a rubber ball) on the hollow inside of the hemisphere, and the wound drainage tube is connected to the internal volume of the pump (preferably through the top of the rigid hemisphere). The weight pulls a negative pressure as the ball returns back to the shape of a sphere.

Another embodiment for a gravity governed pump is created by a siphon. The pump enclosure may act as a collection chamber; however, a separate collection chamber may exist in series with the pump. The pressure pulled is equal to:

$$\text{rho} * g * h \qquad (2)$$

wherein rho is the density of the fluid in the column, g being the gravitational constant, and h being the height of the column). The fluid should be compatible with the wound (such as saline), unless a check valve is used to assure separation of the pump fluid from the wound cavity. The pump can be configured in two ways, depending on the patient situation and the desired pressure:

1. The pump can include a column of fluid that exists in a tube directly connected to the wound. The lower (preferably closed-expandable) container of fluid can rest at the desired height on a separate mechanism (such as a hanging hook or floor), or could be attached to a lower extremity of the patient, again at the desired height. The diameter of the tube would determine the pressure gradient: the larger the diameter, the lower the pressure gradient as fluid is collected.

2. The pump can include two bodies of fluid with a tube from the higher body of fluid to the wound. The mobility of the patient would be determined by the tube length and the mechanism used to carry the pump (for instance, a rolling stand could be used). The diameter of the higher container would determine the pressure gradient: the larger the diameter, the lower the pressure gradient as fluid is collected.

Integrating the spring governed pumps with the gravity governed concept allows for further performance. Then, the magnitude of negative pressure a spring governed pump can obtain is not completely limited by the material properties of the container, the design, and the spring constant combination. Additional weights can be attached to one end of the pump in series with the spring, in order to pull a higher negative pressure. (For the bladder concept, portions of the bladder may need structural support, so that the bladder does not collapse on itself as the weight acts on it.) The weights should be attached between the pump and ground. Even though in this form the orientation of the pump should be maintained, varying the additional weight is a simple solution to achieving multiple pressures beyond that of the original pump properties.

A container evacuation pump is not continuously governed by a force exerted on the container. Instead, the pump is simply an evacuated rigid chamber that is continuously monitored through a pressure gauge, such as gauge 4 in FIGS. 31 and 32. Alternatively, a mechanical check gauge would be used, with an optimal pressure range. When the vacuum pressure decreases to a certain, predetermined level, a notification mechanism is activated and the rigid chamber is recharged. Recharging can be by a pump or by human suction. In this embodiment, the rigid chamber can act as the collection container, or a separate non-structural, expandable container can be inserted into the rigid chamber that is directly connected to the wound drainage tube. An expandable collection chamber can be integrated into any of the mechanical pump concepts disclosed in this disclosure, in order to collect the fluid inside the pump body, acting as a collection liner instead of a completely separate collection canister.

To administer NPWT, the pump is connected to the wound drainage tube, and the container is then evacuated. Air leaks and wound drainage rate determines the pressure gradient, and the pressure range is determined by the maximum pressure pumped and the recharge notification pressure. The maximum pressure pumped can be limited by a pressure activated inlet valve.

As generally applies to all of the above-mentioned pumps, a sequence of steps should be followed. First, the tube connected directly to the dressing should be clamped shut between the dressing and the collection chamber, preferably at the collection chamber end. Then, the pump and collection chamber should be disconnected. If necessary, the collection chamber should be emptied, and/or the proper sterilization procedures should be performed; component 8, FIG. 31, represents a rubber plug, not shown because integral floor 260 is utilized instead, for increased access to the interior of the collection chamber in an alternative construction. The pump should then be reset, and the pump and collection chamber reconnected to the tube. Remove the clamp to begin NPWT again. If a dressing change is also desired, there is no need to use a clamp to keep the dressing sealed. Also, if the collection chamber does not need to be emptied and/or sterilized, then the tube should be clamped between the dressing and the pump, preferably after the collection chamber if it is separate from the pump at the pump end of the tube.

An air leak test can be incorporated into the mechanical pumps, except for the first (1) siphon concept. In the second (2) siphon concept, the higher container is turned upside-down for the initial air leak test. Most air leaks originate at the dressing interfaces. In a purely mechanical pump, air leaks fill the limited volume, causing the maximum time between pump resets to decrease. To eliminate these air leaks and create a reliable, repeatable therapy, devices according to the present disclosure may include an air leak test. By using the air leak test, the purely mechanical pumps have been proven to be capable of lasting throughout the recommended timeframe between dressing changes (3 days). However, this test is not necessary for the occlusive seals and dressings disclosed in this disclosure, but can provide a visual reassurance to the caregiver and patient that the dressing was applied properly and no significant leaks exist in the system.

The air leak test is in the collection chamber. The tube from the wound that enters into the collection chamber enters into a wound compatible solution (such as saline). When applying the NPWT, one should confirm that the end of the tube is submerged in the solution and should look at the solution for air bubbles B, FIGS. 31 and 32, (any air that initially exists in the tube may create air bubbles; therefore, one should wait about 1-2 seconds for additional air bubbles). If air bubbles are detected, the dressing should be sealed until no air bubbles are detected. This resealing may be to completely redress the wound, to smooth out the air leaks in the current dressing, or to reinforce the current dressing with additional dressing components. Once no air bubbles are detected, the pump may need to be reset depending on how much air entered into the pump.

A safety feature of the collection chamber is to limit the amount of liquid capable of being collected. If the collected liquid were blood due to destruction of a vein or artery, there exists a possibility that the patient may die due to fatal bleeding. The collection chamber should be limited to less than 300 cc of liquid to keep the patient at a safe range from possible exsanguination. Therefore, if the pump design can pull more than 300 cc of fluid, a safety feature should be implemented. If the pump acts as the collection chamber, the safety feature should limit its expansion volume. This can be done in various ways through the introduction of limiting, internal (FIG. 31, component 6) and/or external (FIG. 31, component 7) structural components. If an external collection chamber exists, then a safety feature should stop the negative pressure after 300 cc is collected. This can be done by "plugging" the system with a mechanism, such as a float-stop valve.

Prior to the existence of a truly occlusive dressing, a benefit in the external collection chamber was that the pump can be larger than 300 cc, and therefore, account for more air leaks into the system. However, with a truly occlusive dressing, the benefits include that the external collection chamber and its fluids can be easily removed for lab testing purposes, and the pump requires a less rigorous cleaning procedure between dressing changes. However, these benefits are more readily solved with a volume specific container with no rigidity, and containing no initial volume of fluid that may contaminate a exudate sample, if desired, that can be inserted into any of the mechanical pump concepts disclosed in this disclosure, in order to collect the fluid inside the pump body, acting as a collection liner instead of a completely separate collection canister. The 300 cc limitation is recommended for the average adult; however, the limitation volume may vary based on the patient. This volume variation can be designed into multiple pump or collection chamber sizes, or into a single, limit adjustable pump or collection chamber.

Another pump safety feature is a one-way valve incorporated in the tube between the wound and the collection chamber, such as component 2, FIGS. 31 and 32. This mechanism assures that fluid from the pump and collection chamber does not flow back into the dressing. It also can be used as the tube clamping mechanism for resetting the pump or emptying the collection chamber, depending on placement in the tube. This mechanism can also be incorporated into the tube connector on the collection chamber.

Another mechanism that may be included is used to evacuate the initial air found in the system after no air leaks are detected. The current method is to clamp the tube near the pump and to reset the pump until the initial air is evacuated from the system. This can also be accomplished by including a one-way-valve incorporated into the tube connector on the pump, such as component 2, FIGS. 31 and 32, and another one-way-valve incorporated between the interior cavity of the pump and atmosphere, component 3, shown with a cap C in FIG. 31. With this design, one can continue to compress (reset) the pump until the desired vacuum is maintained; the system does not need to be disconnected. The one-way-valve open to atmosphere can be capped after therapy begins.

This mechanism cannot be easily integrated to eliminate the need for resetting the pump in the design that includes a rubber balloon that is inserted into an orifice of an air-tight container and the two siphon pumps. For the balloon design, a connection to the container can be made to incorporate the attachment of a separate pump with the one-way-valve and check valve design. This pump can be attached for initial balloon inflation and container evacuation, and then detached between dressing changes. In the two siphon concepts, a pump can be attached to evacuate the space above the column of fluid, raising the fluid level to the desired height. The pump can be detached for extended therapy, between dressing changes.

An individual sealant component may be packaged by itself to make any skin dressing occlusive. Alternatively, the sealant can be packaged as part of a mechanical NPWT kit, including a mechanical pump and its pre-attached components, tubing with flexible foot and pre-attached tubing connector and optional one way valve, dressing adhesive film to cover the packing material (if necessary), the sealant material in a handheld spray container, a wound packing material, and skin prep (if necessary). Additionally, if there is an adhesive dressing tape-like film that should be handled by the caregiver, then non-stick fingertip covers maybe included for better adhesion outcomes. Non-powdered gloves may also be included, so that the Van der Waals forces for sealant attachment are not altered due to powder on the skin surface. One skilled in the art would realize that kit components may be swapped for their different functional embodiments, discussed above. Also, additional components may be added or put into additional kits that are used in typical dressing changes, such as wound debridement tools, or additional wound therapies, such as medications with their corresponding introduction and (potentially) removal ports through the dressing, into the wound cavity.

As many dressing systems are identified in this disclosure, one skilled in the art would realize that the liquid sealing method can be used in combination with any tissue (a.k.a., skin) dressing in order to create an air-tight seal. As many pumps are identified in this disclosure, one skilled in the art would realize that any pump combined with the occlusive dressing systems would have similar performance characteristics.

One technique according to the present invention for constructing an occlusive dressing over a wound includes at least one of (1) packing the wound with a fluid-pervious material and (2) covering at least a portion of the wound with a protective material. The method further includes applying, such as by spraying, an organic material, preferably elastomeric, that is in a liquid state, and is at least partially cross-linked at least after one of drying and curing, over the packed material and onto skin surrounding the wound to create an occlusive drape as a thin sheet substantially impervious to fluid transfer, having a first, inner surface and a second, outer surface. As utilized herein, the term "organic material" includes matter in various forms that include carbon atoms, including silicone rubbers. The method includes at least one of drying and curing the elastomeric material within thirty minutes after application of the elastomeric material as a layer.

Figure 38:
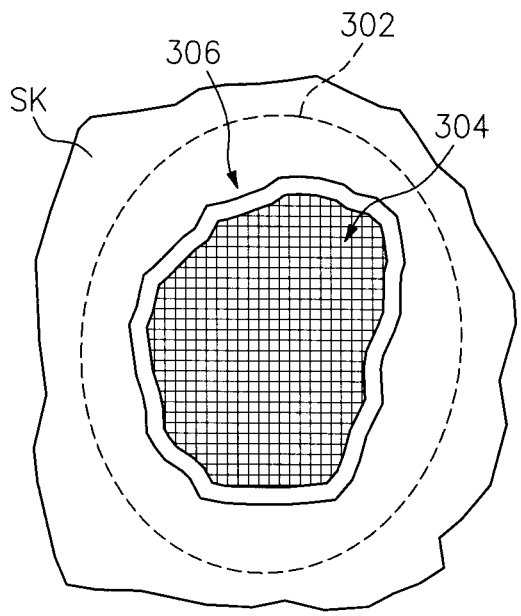
FIG. 38 is a schematic top plan view of the wound shown in FIG. 14 with the additional step of applying a protective covering over the wound.

FIG. 38 is a schematic top plan view of the wound shown in FIG. 14, here with a cleaned skin zone indicated by dashed line 302 and with packing material 304, such as gauze or a sponge. Additionally, a protective covering material 306 is applied over the wound when intended liquid drape material has a sufficiently lower viscosity and longer set time to be absorbed into the packing material 304. Protective material 306 prevents liquid drape material from flowing into the wound cavity. In some constructions, protective material 306 is a solid impermeable or semi-permeable polymeric sheet, which may be utilized with or without adhesive. In other constructions, protective material 306 is a clay-like substance that can be molded and packed over packing material 304 and around a tube inserted into the packing material 304.

Figure 39:
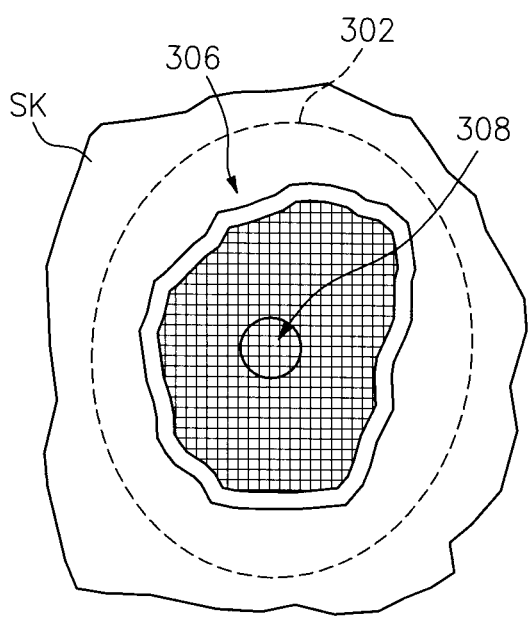
FIG. 39 is a view of FIG. 38 with a hole cut in the protective covering.

FIG. 39 is a view of FIG. 38 with a hole 308 cut in the protective covering 306, if an opening in the protective covering 306 has not already been formed or maintained.

Figure 40:
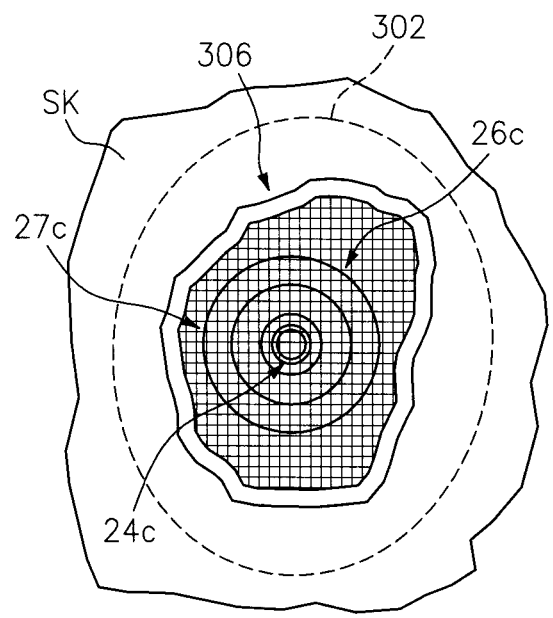
FIG. 40 is a view of FIG. 39 with a tube assembly placed over the hole.

FIG. 40 is a view of FIG. 39 with a tube assembly 27*c*, with tube 24*c* and flange 26*c*, having sleeve 52*d*, rotation region 54*d* and adhesion region 56*d*, placed over the hole 308. Tube assembly 27*c* is maintained in position with adhesive in some techniques and, in other techniques, is manually held in place. Alternatively, tube 24*c* can directly puncture protective covering 306 such that covering 306 maintains a tight seal around tube 24*c*, potentially with an additional seal barrier such as clay or adhesive. In another construction, flange 26*c* is sufficiently large in diameter to completely cover the wound.

Figure 41:
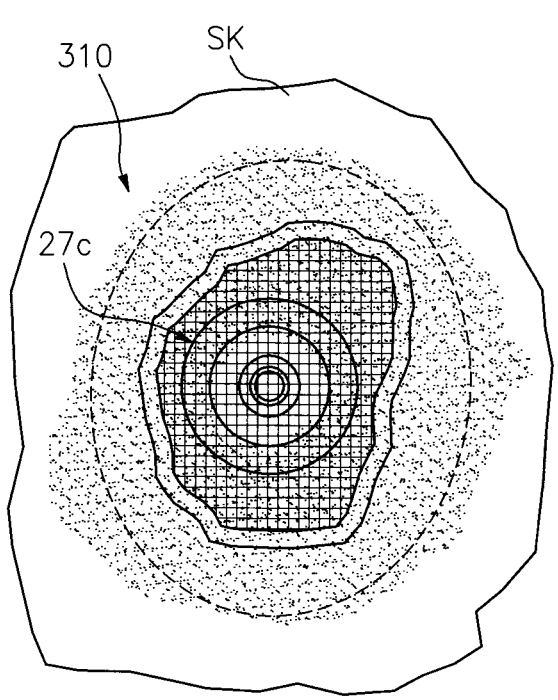
FIG. 41 is a view of FIG. 40 with liquid drape material applied over the protective covering and onto surrounding skin to construct a dressing according to the present invention.
Figure 42:
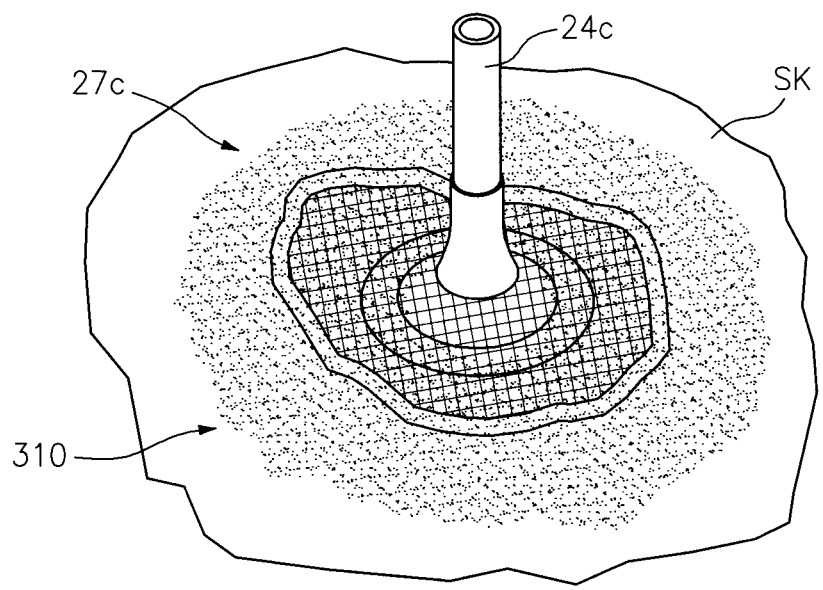
FIG. 42 is a schematic perspective view of the dressing of FIG. 41.

FIG. 41 is a view of FIG. 40 with liquid drape material 310 applied over the protective covering 306 and onto surrounding skin SK to cover skin zone 302 to thereby construct a dressing according to the present invention. The liquid drape material 310 is applied by spraying or application technique such that material 310 firmly attaches to skin SK surrounding the wound and covers any protective cover layer 306, if utilized, as well as creating an air-tight seal around flange 26*d*. FIG. 42 is a schematic perspective view of the dressing of FIG. 41 In other constructions, the drape is constructed directly onto a tube without utilizing a separate flange.

FIG. 43 is a schematic perspective view of a novel flange 26*d* according to the present invention with integral connector 320 having a barb-type engagement feature 322 defining passage 324. Engagement feature 322 is insertable into end of a tube.

Although specific features of the present invention are shown in some drawings and not in others, this is for convenience only, as each feature may be combined with any or all of the other features in accordance with the invention. While there have been shown, described, and pointed out fundamental novel features of the invention as applied to one or more preferred embodiments thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto. Other embodiments will occur to those skilled in the art and are within the following claims.

What is claimed is:

1. A kit suitable for occlusively sealing a wound penetrating the skin of a patient, comprising:
    a drape formed as a thin sheet of an organic material substantially impervious to fluid transfer and having a first surface on one side of the drape and a second surface on an opposite side of the drape and having an outer edge;
    at least one connection interface component capable of connecting with a source of negative pressure, the at least one connection interface component including at least one of (i) a flexible tube having a first end extendable through the drape and having a second end connectable with the source of negative pressure, (ii) at least two pieces of drape capable of forming a joint through which a first end of a tube is insertable, (iii) a flange having a central passage and connectable with a tube, and/or (iv) a tube connector;
    at least one biocompatible adhesive that is at least one of (1) disposed on at least a portion of the first surface of the drape and/or (2) capable of contacting at least a portion of at least the first surface of the drape;
    when the kit includes the at least one biocompatible adhesive disposed on at least a portion of the first surface of the drape, the kit further includes at least a first removable liner covering at least a portion of the at least one biocompatible adhesive on the first surface of the drape; and
    at least one container of at least one dressing-to-skin interface sealant component that is capable of being delivered as a sealant in a liquid state at pre-selected ambient conditions, the sealant as delivered (A) being at least partially cross-linked after at least one of drying and/or curing, (B) being capable of at least one of drying and/or curing within thirty minutes after application of the sealant to create a dressing-to-skin air-tight interface when applied as an air-tight layer of sealant over the outer edge of the drape after the drape is applied to the skin surrounding the wound with the first surface of the drape facing the skin and (C) being capable of occlusively bonding to the second surface of the drape and skin surrounding the drape after the drape is applied to the skin surrounding the wound.

2. The kit of claim 1 further including a mechanical pump capable of serving as the source of negative pressure.

3. The kit of claim 2 wherein the mechanical pump is a bellows-type pump capable of being rolled upon itself and then unrolling to exert negative pressure.

4. The kit of claim 2 wherein the mechanical pump includes a pressure activated inlet valve capable of limiting the maximum negative pressure applied by the mechanical pump after the mechanical pump is connected to the drape.

5. The kit of claim 1 further including at least one sealant applicator.

6. The kit of claim 5 wherein the at least one sealant applicator is a sponge.

7. The kit of claim 5 wherein the at least one sealant applicator is a spraying device.

8. The kit of claim 1 wherein adhesive is disposed on at least a majority of the second surface of the drape.

9. The kit of claim 8 wherein the drape includes at least one removable liner covering at least one of at least a portion of (1) the second surface of the drape and/or (2) adhesive disposed on the second surface of the drape.

10. The kit of claim 1 wherein the at least one connection interface component includes the flexible tube having the first end defining an opening.

11. The kit of claim 10 wherein the first end of the flexible tube includes a feature in addition to the opening to resist blockage of the flexible tube, wherein the feature to resist blockage of the flexible tube is a helical cut and/or a separate geometric extension attached to the flexible tube.

12. The kit of claim 1 wherein the sealant as delivered cures through an evaporation process.

13. The kit of claim 12 wherein the evaporation process is the evaporation of water from the sealant as delivered.

14. The kit of claim 1 wherein the organic material and the sealant as delivered after at least one of drying and/or curing are elastomeric.

15. The kit of claim 1 wherein the drape and the sealant as delivered are each substantially derived from a material, which is the same material for both the drape and the sealant.

16. The kit of claim 1 wherein at least a majority of each of the drape and the sealant as delivered are each derived from a latex compound.

17. The kit of claim 1 wherein at least a majority of each of the drape and the sealant as delivered are each derived from a silicone compound.

18. The kit of claim 1 wherein at least one of the at least one biocompatible adhesive is a silicone-based adhesive.

19. The kit of claim 1 wherein the at least one connection interface component includes the flange having at least one of (1) an adhesive region, a sleeve region defining the central passage through which a first end of a tube is insertable, and a rotation region that allows the tube to connect perpendicular to the skin surface and to be oriented in any orientation after the drape is applied to the skin surrounding the wound, and/or (2) an adhesive region, a sleeve region defining the central passage capable of communicating with a connector capable of mating with a first end of a tube, and a rotation region that allows the tube to connect perpendicular to the skin surface and to be oriented in any orientation after the drape is applied to the skin surrounding the wound.

20. The kit of claim 1 wherein at least one of the at least one container of at least one dressing-to-skin interface sealant component is a cartridge removably insertable into a dispensing apparatus.

21. The kit of claim 1 wherein at least one of the at least one container of at least one dressing-to-skin interface sealant component is squeezable to deliver the sealant.

22. The kit of claim 1 further including at least one wound packing material.

23. The kit of claim 1 wherein at least one of the at least one biocompatible adhesive is an acrylic-based adhesive that is disposed on and bonded to at least a portion of the first surface of the drape that includes at least a portion of the outer edge of the drape.

24. The kit of claim 1 wherein the sealant as delivered, after the at least one of drying and/or curing, is capable of accommodating tensional strain reached at the skin surface during large deformation body movements while remaining air-tight, including accommodating large deformation strain of approximately 0.45 in tension.

25. The kit of claim 1 wherein the sealant as delivered, after the at least one of drying and/or curing, includes at least one rubber polymer selected from the group of latex materials, natural rubber, biorubber, synthetic rubber, hypoallergenic latex, nitrile rubber, neoprene, silicones and polyurethanes.

26. The kit of claim 1 further including at least a second container of at least one separate sealant additive.

27. The kit of claim 1 further including at least one of (1) a non-stick handling component and/or (2) a handling tab, wherein the at least one of (1) the non-stick handling component and/or (2) the handling tab is at least one of (a) at least one separate component from any removable liner and/or (b) at least one separate component integrated into at least one removable liner and removable from the at least one removable liner for use as a separate component.

28. The kit of claim 1 further including at least one purge valve that is capable of causing a controlled, temporary air leak between the drape and the wound, wherein the drape is constructed to be applied to the skin surrounding the wound to create a sealed volume under the drape in fluid communication with the source of negative pressure, and wherein the controlled, temporary air leak flows from outside of the sealed volume and is capable of causing liquid between the drape and the wound to flow towards the source of negative pressure.

29. The kit of claim 1 wherein the sealant as delivered is formulated with at least one of a natural rubber latex and/or a biorubber emulsion.

30. The kit of claim 1 further including at least one port suitable for at least one of insertion and/or removal of at least one of a fluid and/or a medication between the drape and the wound after the drape is applied to the skin surrounding the wound, wherein the at least one port is a physically separate component from any connection interface component that allows the drape to be connected to the source of negative pressure after the drape is applied to the skin surrounding the wound.

31. The kit of claim 1 wherein the sealant is formulated to occlusively seal over at least the outer edge of the drape by bonding with Van der Waals forces and with no other chemical bonds to both the skin and second surface of the drape as a continuous layer over the outer edge, after the drape is applied to the skin surrounding the wound and after the sealant is at least partially cross-linked after at least one of drying and/or curing.

32. The kit of claim 1 wherein the sealant is formulated to have a low viscosity when the sealant is being delivered as a sealant in a liquid state, enabling it to conform to all contact surfaces during application of the sealant, including any folds and/or creases in the skin, making the sealant capable of being occlusively applied such that (i) no air leak channels at the outer edge are present after application of the sealant and (ii) all contact surfaces of the sealant are completely wet by the sealant after application of the sealant.

33. The kit of claim 1 wherein the sealant at least one of dries and/or cures into a film and/or sheet.

34. The kit of claim 1 wherein the sealant after at least one of drying and/or curing is derived from at least one type of rubber compound that is not silicone-based.

35. The kit of claim 1 wherein the sealant is capable of at least one of drying and/or curing within one minute after application of the sealant.

36. A kit suitable for occlusively sealing a wound penetrating the skin of a patient, comprising:
 a drape formed as a thin sheet of an organic material substantially impervious to fluid transfer and having a first surface on one side of the drape and a second surface on an opposite side of the drape and having an outer edge;
 at least one biocompatible adhesive that is at least one of (1) disposed on at least a portion of the first surface of the drape and/or (2) capable of contacting at least a portion of at least the first surface of the drape;
 when the kit includes the at least one biocompatible adhesive disposed on at least a portion of the first surface of the drape, the kit further includes at least a first removable liner covering at least a portion of the at least one biocompatible adhesive on the first surface of the drape; and
 at least one container of at least one dressing-to-skin interface sealant component that is capable of being delivered as a sealant in a liquid state at pre-selected ambient conditions, the sealant as delivered (A) being at least partially cross-linked after at least one of drying and/or curing, (B) being capable of at least one of drying and/or curing within thirty minutes after application of the sealant to create a dressing-to-skin airtight interface when applied as an air-tight layer of sealant over the outer edge of the drape after the drape is applied to the skin surrounding the wound with the first surface of the drape facing the skin and (C) being capable of occlusively bonding to the second surface of the drape and skin surrounding the drape after the drape is applied to the skin surrounding the wound, wherein at least one of the at least one container of at least one dressing-to-skin interface sealant component is a cartridge removably insertable into a dispensing apparatus.

* * * * *